(12) United States Patent
Akira et al.

(10) Patent No.: US 8,894,996 B2
(45) Date of Patent: Nov. 25, 2014

(54) IMMUNOADJUVANT COMPOSITION AND USE THEREOF

(75) Inventors: Shizuo Akira, Osaka (JP); Osamu Takeuchi, Osaka (JP); Kazufumi Matsushita, Osaka (JP); Ken Ishii, Osaka (JP)

(73) Assignee: Osaka University, Osaka (JP)

( * ) Notice: Subject to any disclaimer, the term of this patent is extended or adjusted under 35 U.S.C. 154(b) by 322 days.

(21) Appl. No.: 13/203,080

(22) PCT Filed: Feb. 26, 2010

(86) PCT No.: PCT/JP2010/053051
§ 371 (c)(1),
(2), (4) Date: Nov. 4, 2011

(87) PCT Pub. No.: WO2010/098429
PCT Pub. Date: Sep. 2, 2010

(65) Prior Publication Data
US 2012/0070452 A1 Mar. 22, 2012

(30) Foreign Application Priority Data
Feb. 27, 2009 (JP) ................... 2009-046990

(51) Int. Cl.
| | | |
|---|---|---|
| *A01N 61/00* | (2006.01) | |
| *A61K 31/00* | (2006.01) | |
| *A61K 39/00* | (2006.01) | |
| *A61K 36/38* | (2006.01) | |
| *A61K 39/395* | (2006.01) | |
| *A61K 45/00* | (2006.01) | |
| *A61K 47/00* | (2006.01) | |
| *C07H 21/02* | (2006.01) | |
| *C07H 21/04* | (2006.01) | |
| *A61K 39/39* | (2006.01) | |
| *A01K 67/027* | (2006.01) | |
| *A61K 45/06* | (2006.01) | |
| *C12N 9/22* | (2006.01) | |
| *C12N 15/85* | (2006.01) | |

(52) U.S. Cl.
CPC ............ *A61K 39/39* (2013.01); *A01K 67/0276* (2013.01); *A61K 31/00* (2013.01); *A61K 45/06* (2013.01); *C12N 9/22* (2013.01); *C12N 15/8509* (2013.01); *A01K 2217/075* (2013.01); *A01K 2227/105* (2013.01); *A01K 2267/0325* (2013.01); *A01K 2267/035* (2013.01); *A01K 2267/0381* (2013.01); *A01K 2267/0387* (2013.01); *A61K 2039/55516* (2013.01)
USPC ............. 424/130.1; 424/139.1; 424/158.1; 424/184.1; 424/278.1; 514/1; 514/1.1; 536/23.1; 536/24.5

(58) Field of Classification Search
None
See application file for complete search history.

(56) References Cited

U.S. PATENT DOCUMENTS

| | | | |
|---|---|---|---|
| 2007/0142288 A1* | 6/2007 | Kolattukudy et al. | ......... 514/12 |
| 2010/0247568 A1 | 9/2010 | Tsukui et al. | |

FOREIGN PATENT DOCUMENTS

| | | |
|---|---|---|
| JP | 2008-100919 | 5/2008 |
| WO | 2009/057763 | 5/2009 |
| WO | 2010/126605 | 11/2010 |

OTHER PUBLICATIONS

Niu et al. 'Monocyte Chemotactic Protein (MCP)-1 Promotes Angiogenesis via a Novel Transcription Factor, MCP-1-induced Protein (MCPIP)*,' J. Biol. Chem. 283(21):14542-14551, 2008.*
Akira et al. 'Regnase-1, a Ribonuclease Involved in the Regulation of Immune Responses.' Cold Spring Harb Symp Quant Biol published online Oct. 25, 2013, pp. 1-10.*
Extended European Search Report issued Nov. 7, 2012 in corresponding European Application No. 10746308.5.
Skalniak, Lukasz, et al., "Regulatory feedback loop between NF-κB and MCP-1 induced protein 1 RNase", The FEBS Journal, vol. 276, No. 20, Oct. 2009, pp. 5892-5905.
Akira, Shizuo, et al., "PL2-1 Zc3h12a, a negative regulator in the TLR response", Cytokine, vol. 48, Nos. 1-2, Oct. 2009, p. 4.
Cifuentes, Ricardo A., et al., "*ZC3H12A* (MCPIP1): Molecular characteristics and clinical implications", Clinica Chimica Acta, vol. 411, Nos. 23-24, Dec. 2010, pp. 1862-1868.
English translation of the International Preliminary Report on Patentability dated Sep. 13, 2011 along with the Written Opinion.
Toshimi Sudo et al., "Cancer Cell Therapy with HER2-Specific Monoclonal Antibody", Biotherapy, vol. 19, No. 5, p. 430-434, Sep. 2005.
Terumasa Hisano et al., "Reinforcement Tumor Immunotherapy Using RNF43 Peptide Pulse Dendritic Cells and Activated CTL Clone for Advanced Solid Tumor Patient", Biotherapy, vol. 22, No. 5, p. 332-337, Sep. 2008.
J.U. Igietseme et al., "Protection of mice from herpes simplex virus-induced retinitis by in vitro-activated immune cells", J. Virol., vol. 63, No. 11, p. 4808-4813, Nov. 1989.
International Search Report issued Apr. 6, 2010 in International (PCT) Application No. PCT/JP2010/053051.
J. Liang et al., "A Novel CCH-Zinc Finger Protein Family Regulates Proinflammatory Activation of Macrophages", The Journal of Biological Chemistry, vol. 283, No. 10, pp. 6337-6346, Mar. 7, 2006.
J. Niu et al., "Monocyte Chemotactic Protein (MCP)-1 Promotes Angiogenesis Via a Novel Transcription Factor, MCP-1-Induced Protein (MCPIP)", The Journal of Biological Chemistry, vol. 283, No. 21, pp. 14542-14551, Mar. 23, 2008.
K. Matsushita et al., "Zc3h12a is an RNase Essential for Controlling Immune Responses by Regulating mRNA Decay", Nature, vol. 458, No. 7242, pp. 1185-1190, Apr. 30, 2009.

* cited by examiner

*Primary Examiner* — Nora Rooney
(74) *Attorney, Agent, or Firm* — Wenderoth, Lind & Ponack, L.L.P.

(57) ABSTRACT

Disclosed is a composition comprising, as an active ingredient, at least one selected from the group consisting of a Zc3h12a gene inhibitor and a Zc3h12a protein inhibitor. This composition can be used as an immunoadjuvant.

3 Claims, 17 Drawing Sheets

IMMUNOADJUVANT COMPOSITION AND USE THEREOF

This application is a U.S. national stage of International Application No. PCT/W2010/053051 filed Feb. 26, 2010.

TECHNICAL FIELD

The present invention relates to an immunoadjuvant composition, a vaccine composition, a process for immunizing a non-human animal, an activated immune cell preparation, and a production process for the preparation.

BACKGROUND ART

Adjuvants administered as a mixture with vaccine antigens activate natural immunity and help the induction of antigen-specific immune response via antigen presentation.

Various adjuvants for animal experiments are known. Common compounds of non-biological origin are used as adjuvants due to their properties of adsorbing antigens such as pathogens, and examples of such a compound include sodium hydroxide, aluminum hydroxide, calcium phosphate, alum, and a carboxyvinyl polymer. However, these precipitating adjuvants are prone to cause injection site induration. Oily substances such as liquid paraffin, lanolin, and Freund's adjuvant are also used as adjuvants due to their properties of encapsulating an aqueous antigen solution and forming micelles. However, since a mixture of such an oil-based adjuvant and a vaccine antigen forms an emulsion containing micelles, the mixture has a high viscosity, which may cause injection pain, and is prone to cause injection site induration.

Besides the above adjuvants, a relatively safe bacterium *Mycobacterium bovis* (BCG), which hardly causes endotoxin shock or the like, is also used as an adjuvant. However, BCG bacterial bodies are prone to cause an ulcer at the injection site.

Since a highly effective adjuvant generally has a strong toxicity, development of a safe and effective adjuvant has been desired.

JP-2008-100919-A describes, as an adjuvant of natural product origin, a nucleic acid/polysaccharide complex composed of a CpG oligonucleotide having a natural phosphodiester backbone and a poly(dA) tail and of a β-1,3-glucan having a molecular weight of 25000 or more. This patent literature suggests that this nucleic acid/polysaccharide complex can promote production of cytokines and antibodies that establish dominance of Th1 cell activity and therefore the complex can be used as an immunoadjuvant.

SUMMARY OF INVENTION

Technical Problem

A principal object of the present invention is to provide a novel immunoadjuvant composition.

Solution to Problem

The inventors conducted extensive researches in order to solve the above problems and obtained the following findings.

(i) A homo knockout mouse in which the Zc3h12a gene had been destroyed (Zc3h12a$^{-/-}$ mouse) showed an increased number of plasma cells and infiltration of plasma cells to the lung. The Zc3h12a$^{-/-}$ mouse also showed augmented serum immunoglobulin levels and autoantibody production.

(ii) Most Zc3h12a$^{-/-}$ splenic T cells showed effector/memory characteristics and produced interferon-γ in response to T-cell receptor stimulation. Thus, destruction of Zc3h12a activated the acquired immune system and, as a result, the numbers of plasma cells and memory T cells increased.

(iii) Macrophages from the Zc3h12a$^{-/-}$ mouse showed highly increased production of IL-6 and IL-12p40 in response to TLR (Toll-like receptor) ligands. In contrast, production of TNF was not significantly increased in response to TLR ligands. Thus, destruction of Zc3h12a increased production of particular cytokines.

(iv) Zc3h12a protein has a zinc finger region and binds to RNA.

(v) The Zc3h12a gene contains a putative N-terminal nuclease domain, and the expressed protein had ribonuclease activity. Whereas degradation of a particular mRNA contributes to maintenance of its homeostasis, the absence of Zc3h12a ribonuclease activity in the Zc3h12a$^{-/-}$ mouse inhibits degradation of mRNA for molecules including particular cytokines and increases production of the molecules.

(vi) Taken together, these findings indicate that a Zc3h12a gene inhibitor or a Zc3h12a protein inhibitor can be suitably used as an immunoadjuvant.

The present invention has been completed based on the above findings and provides the following immunoadjuvant composition, vaccine composition, activated immune cell preparation, and production process for the preparation.

(1) An immunoadjuvant composition comprising, as an active ingredient, at least one selected from the group consisting of a Zc3h12a gene inhibitor and a Zc3h12a protein inhibitor.

(2) The immunoadjuvant composition according to (1), further comprising another immunoadjuvant.

(3) A vaccine composition comprising a vaccine antigen and at least one selected from the group consisting of a Zc3h12a gene inhibitor and a Zc3h12a protein inhibitor.

(4) The vaccine composition according to (3), further comprising another immunoadjuvant.

(5) A process for immunizing an animal, comprising administrating to a non-human animal the vaccine composition according to (3) or (4).

(6) A production process for an activated immune cell, comprising the step of bringing an immune cell harvested from a subject into contact with at least one selected from the group consisting of a Zc3h12a gene inhibitor and a Zc3h12a protein inhibitor, thereby activating the immune cell.

(7) An activated immune cell produced by the process according to (6).

(8) A compound for enhancing the immunogenicity of a vaccine antigen, the compound being at least one selected from the group consisting of a Zc3h12a gene inhibitor and a Zc3h12a protein inhibitor.

(9) A use of a compound for producing an immunoadjuvant, the compound being at least one selected from the group consisting of a Zc3h12a gene inhibitor and a Zc3h12a protein inhibitor.

(10) A process for enhancing the immunogenicity of a vaccine antigen, comprising the step of mixing the vaccine antigen with at least one selected from the group consisting of a Zc3h12a gene inhibitor and a Zc3h12a protein inhibitor.

(11) A composition for activating immunity, the composition comprising a vaccine antigen and at least one selected from the group consisting of a Zc3h12a gene inhibitor and a Zc3h12a protein inhibitor.

(12) A use of a composition comprising a vaccine antigen and at least one selected from the group consisting of a Zc3h12a gene inhibitor and a Zc3h12a protein inhibitor, for producing a vaccine composition.

Advantageous Effects of Invention

The immunoadjuvant composition of the present invention inhibits the function of the Zc3h12a gene or Zc3h12a protein, thereby activating acquired immunity as well as natural immunity. Whereas most of conventional adjuvants activate only natural immunity, the immunoadjuvant composition of the present invention serves as a powerful adjuvant that activates not only natural immunity but also acquired immunity.

In addition, since the immunoadjuvant composition is a Zc3h12a gene inhibitor or a Zc3h12a protein inhibitor, the immunoadjuvant composition can be designed as a nucleic acid such as siRNA, a low-molecular compound, or the like, and is therefore highly safe.

BRIEF DESCRIPTION OF DRAWINGS

FIG. 24 is the sequence alignments of the N-terminal and CCCH domains in mouse and human Zc3h12a.

FIG. 25 is the structure model of the N-terminal domain of Zc3h12a.

FIG. 26 is the measurement results of the endoribonuclease activity of Zc3h12a.

FIG. 27 is the measurement results of the endoribonuclease activity of Zc3h12a.

DESCRIPTION OF EMBODIMENTS

Figure 1:
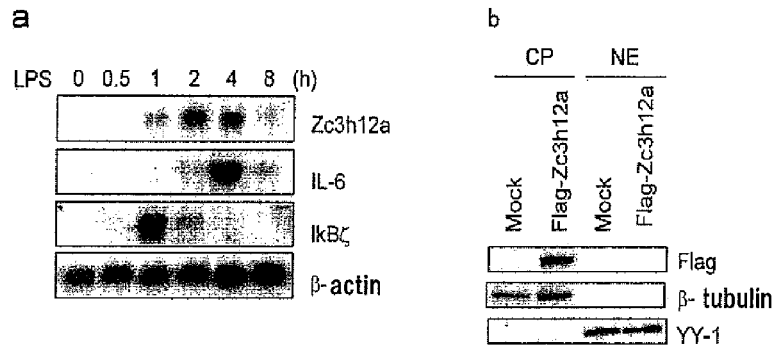
FIG. 1 is the results of Northern blot analysis of genes expressed under LPS induction (LPS-inducible genes) (a) and the results of Western blot analysis for intracellular localization of Zc3h12a (b).

The present invention will be explained in detail below.
(I) Immunoadjuvant Composition The immunoadjuvant composition of the present invention comprises, as an active ingredient, at least one selected from the group consisting of a Zc3h12a gene inhibitor and a Zc3h12a protein inhibitor.
Zc3h12a Gene A Toll-like receptor (TLR) is a receptor that recognizes microbial components and evokes inflammation and immune response. TLR stimulation activates a complex set of gene expressions that regulate the magnitude and duration of immune response. The Zc3h12a gene is an immune response modifier that is inducible by TLR stimulation. The base sequence of the Zc3h12a gene is registered under Accession No. NM_025079 in NCBI.
Zc3h12a Gene Inhibitor The Zc3h12a gene inhibitor may be any substance as long as it inhibits the expression of the Zc3h12a gene, and examples of the inhibitor include a low-molecular compound, a nucleic acid, a protein, and a glycoprotein. Among these, a low-molecular compound is preferred due to its ease of use as a medicine. Also preferred is a nucleic acid such as siRNA, shRNA, or stRNA due to its ease of design and to its low toxicity.

The design methods for siRNA and shRNA are well known and are respectively described in, for example, Elbashir, S. M., Harborth, J., Lendeckel, W., Yalcin, A., Weber, K., and Tuschl, T. (2001). Duplexes of 21-nucleotide RNAs mediate RNA interference in cultured mammalian cells. Nature 411, 494-498; and Paddison, P. J., Caudy, A. A., Sachidanandam, R. & Hannon, G. J. Short hairpin activated gene silencing in mammalian cells. Methods Mol. Biol. 265, 85-100 (2004). siRNA and shRNA can be obtained upon request from ABI, Dharmacon, or the like.

The screening of the Zc3h12a gene inhibitor can be carried out by, for example, the following process: test substances are brought into contact with an assay cell transfected with a Zc3h12a gene expression plasmid and a plasmid in which 3'-UTR for the IL-6 gene or the like is placed downstream of a gene expressing luciferase, a fluorescent protein, or the like; and then, using luciferase assay, fluorescence detection, or the like, the test substances are screened for the ability to decrease the expression of the Zc3h12a gene.

Alternatively, test substances are brought into contact with an assay cell transfected with a Zc3h12a gene expression plasmid containing a regulatory region and a structural gene, and then, using Western blotting, Northern blotting, or the like, the test substances are screened for the ability to decrease the expression of the Zc3h12a gene.

Zc3h12a Protein Inhibitor

The Zc3h12a protein inhibitor may be any substance as long as it inhibits the activity of Zc3h12a protein, and examples of the inhibitor include a low-molecular compound, a nucleic acid, a protein, and a glycoprotein. Among these, a low-molecular compound is preferred due to its ease of use as a medicine.

The screening of the Zc3h12a protein inhibitor may be carried out by, for example, comparing RNA degradation activity levels between assays performed in the presence and absence of test substances, and selecting a substance that reduces RNA degradation activity.

In particular, first, a recombinant human Zc3h12a protein is synthesized as follows. The human Zc3h12a gene (NCBI Accession number: NM_025079) is inserted into a plasmid such as pGEX-6P1, and then *Escherichia coli* BL21-Gold (DE3)pLysS (Stratagene) is transformed with the plasmid to express the protein. After expression of this protein, the cells are collected and re-suspended in PBS. The cells are lysed by sonication followed by addition of Triton X-100 at a final concentration of 1% and incubation for 30 minutes at 4° C. with gentle shaking. The debris is then removed by centrifugation and the supernatant is incubated with Glutathione Sepharose 4B (GE Healthcare) for 30 minutes at 4° C. with gentle shaking. The resins are collected and washed 5 times with PBS and resuspended in PreScission Protease cleavage buffer (50 mM Tris, 150 mM NaCl, 1 mM EDTA and 1 µM DTT). PreScission Protease (GE Healthcare) (80 U) is added and incubated for 4 hours at 4° C. with gentle shaking. The supernatant is collected and stored at −80° C. as a Zc3h12a protein solution.

Next, RNA having a sequence homologous to the sequence of 3'-UTR conserved domain of IL-6 is synthesized using an in vitro transcription method. In the in vitro transcription, RNA labeling is performed using [$^{32}$P]-labeled RNA (5000 cpm).

This labeled RNA and the Zc3h12a protein were mixed in cleavage buffer (25 mM Hepes, 50 mM KOAc, and 5 µM DTT) with or without 5 mM Mg (Oac)$_2$ in the presence of Rnasin plus (40 U) (Promega). The cleaved RNA is purified with TRIzol (InvitroGen) and analyzed by denaturing PAGE using 6% TBE-Urea gel (InvitroGen) and autoradiography. The cleaved RNA is detectable as a RNA that moves faster. Test substances are subjected to this system for the purpose of screening for a substance that reduces the cleavage activity. However, an analysis process for the cleavage activity is not limited thereto.

The screening of the Zc3h12a protein inhibitor can be carried out by a different process from the above. For example, test substances are brought into contact with an assay cell transfected with a Zc3h12a gene expression plasmid and a plasmid in which 3'-UTR for the IL-6 gene or the like is placed downstream of a gene expressing luciferase, a fluorescent protein, or the like; and then, using luciferase assay, fluorescence detection, or the like, the test substances are screened for the ability to decrease the expression of the Zc3h12a gene.

Preparation

The concentration of the above inhibitor in the immunoadjuvant composition of the present invention varies depending on the kind of the inhibitor, but may be, for example, about 10 µg/ml to 100 mg/ml.

The immunoadjuvant composition may be in the form of a sterile aqueous or non-aqueous solution, suspension, or emulsion. The immunoadjuvant composition may further contain a pharmaceutically acceptable diluent, auxiliary, carrier, or the like, for example, a salt, a buffer, or the like.

The immunoadjuvant composition may be intended to be ingested as contained in a food or drink for humans or in a drinking water or feed for animals. That is, the immunoadjuvant composition includes a food or drink composition. The concentration of the inhibitor in a food or drink may be, for example, about 1 µg/ml to 100 mg/ml.

In cases where the inhibitor in the immunoadjuvant composition is a nucleic acid, this inhibitor may be a liposome preparation. A preparing process for a liposome preparation containing a nucleic acid is well known, and such a process is described in, for example, Whitehead K A, Langer R, Anderson D G. Knocking down barriers: advances in siRNA delivery. Nat Rev Drug Discov. 2009 8(2): 129-38.

The immunoadjuvant composition of the present invention may contain, besides the above inhibitor, a known immunoadjuvant. The immunoadjuvant to be combined is not specifically limited, and may be any known immunoadjuvant. Examples of such a known immunoadjuvant include a killed microorganism such as Freund's complete adjuvant and tubercle bacillus, and amla adjuvant. There also included are a nucleic acid/polysaccharide complex composed of a CpG oligonucleotide having a natural phosphodiester backbone and a poly(dA) tail and of a β-1,3-glucan having a molecular weight of 25000 or more; hemozoin; and β-hematin. The concentration of the immunoadjuvant to be combined in the immunoadjuvant composition may be, for example, about 1 µg/ml to 100 mg/ml.

In cases where the immunoadjuvant composition of the present invention contains a plurality of components, the components may be mixed or separately contained.

(II) Vaccine Composition

The inhibitor described above can be combined with a vaccine antigen and made into a vaccine composition. By mixing the inhibitor with a vaccine antigen, the immunogenicity of the vaccine antigen can be enhanced. The vaccine composition may contain, besides the above inhibitor, another known immunoadjuvant.

The kind of the vaccine is not specifically limited and any known vaccine can be used. Examples of the known vaccine include allergy vaccines against a food allergen, a house dust allergen, a pollen allergen such as cedar pollen, or an allergen such as animal hair. Examples of the pollen allergen include cedar pollen allergen (Cry j 1 and Cry j 2), ragweed allergen (Amba1, Amba2, Amba5, Ambt5, and Ambp5), and orchard grass allergen (Dacg2). Examples of the food allergen include casein, lactalbumin, lactoglobulin, ovomucoid, ovalbumin, and conalbumin. Examples of the house dust allergen include mite allergen (Derf1, Derf2, Zen1, Derp1, and Derp2).

The vaccine may be an infection vaccine and examples thereof include an inactivated whole vaccine, a subunit vaccine, and a toxoid. These vaccines can develop immunity in animals against a pathogen such as a bacterium, a virus, a *rickettsia*, and a parasite.

In cases where the infection vaccine is for humans, the vaccine may be against, for example, influenza such as type A and type B, poliovirus, Japanese encephalitis, tubercle bacillus, human papilloma virus, Plasmodium, SARS, avian influenza that can infect humans, typhoid fever, paratyphoid fever, pest, pertussis, or typhus. In cases where the infection vaccine is for non-human animals, the vaccine may be against, for example, equine influenza virus, equine herpesvirus, equine meningoencephalitis virus, foot-and-mouth disease virus, rabies, feline panleukopenia, feline rhinotracheitis, infectious bovine rhinotracheitis, parainfluenza type 3, bovine viral diarrhea, bovine adenovirus, porcine parvovirus, canine adenovirus, canine distemper virus, canine parvovirus, canine parainfluenza, avian influenza, brucellosis, vibriosis, leptospirosis, clostridial infection, or salmonellosis.

The vaccine used in the present invention may be a cancer vaccine. The cancer vaccine is not specifically limited and may be a known vaccine. The cancer vaccine may be, for example, a WT-1 vaccine, a HER2/neu vaccine against breast cancer, a MAGE vaccine against malignant melanoma, or a CEA vaccine against colon cancer.

The vaccine composition may be in the form of a sterile aqueous or non-aqueous solution, suspension, or emulsion. The vaccine composition may further contain a pharmaceutically acceptable diluent, auxiliary, carrier, or the like, for example, a salt, a buffer, or the like.

The concentration of the inhibitor in the vaccine composition may be, for example, about 10 µg/ml to 100 mg/ml. In cases where the vaccine composition is combined with an immunoadjuvant other than the immunoadjuvant of the present invention, the concentration of the immunoadjuvant to be combined may be, for example, about 1 µg/ml to 100 mg/ml. The concentration of the vaccine in the vaccine composition may be, for example, about 1 µg/ml to 100 mg/ml.

The vaccine composition of the present invention includes a food or drink composition. In cases where the vaccine composition is a food or drink composition, the concentration of the inhibitor in the composition may be, for example, about 1 µg/ml to 100 mg/ml. In cases where the vaccine composition is combined with an immunoadjuvant other than the immunoadjuvant of the present invention, the concentration of the immunoadjuvant to be combined may be, for example, about 1 µg/ml to 100 mg/ml. The concentration of the vaccine in the food or drink composition may be, for example, about 1 µg/ml to 100 mg/ml.

In cases where the vaccine composition contains a plurality of components, the components may be mixed or separately contained.

(III) Use of Immunoadjuvant Composition or Vaccine Composition

The vaccine composition described above can be administered as a mixture of the immunoadjuvant composition and the vaccine antigen. Alternatively, the immunoadjuvant composition and the vaccine antigen can be separately administered. By administration of the vaccine composition, an animal can be immunized. That is, the immunity (acquired immunity and natural immunity) of an animal can be activated. In cases where the immunoadjuvant composition contains the above inhibitor and another immunoadjuvant, these adjuvants may be separately administered or may be administered as a mixture. In cases where the immunoadjuvant composition or vaccine composition of the present invention is a medicinal composition, the composition can be therapeutically administered. In cases where the immunoadjuvant composition or vaccine composition is a food composition, the composition can be non-therapeutically administered.

The immunoadjuvant composition or vaccine composition of the present invention can be administered to any animal (a human or a non-human) that has an immune system. Examples of the animal include mammals such as humans, monkeys, cattle, horses, pigs, sheep, goats, dogs, cats, guinea pigs, rats, and mice; and birds such as chickens, ducks, and geese.

In particular, the immunoadjuvant composition or vaccine composition of the present invention is useful as an allergy vaccine or infection vaccine for humans, an allergy vaccine or infection vaccine for pets such as dogs and cats, or an infection vaccine for farm animals such as cattle, pigs, and chickens.

The immunoadjuvant composition or vaccine composition can be inoculated orally, intramuscularly, intradermally, subcutaneously, intranasally, endotracheally, percutaneously, or via other routes. The immunoadjuvant composition or vaccine composition of the present invention, as described above, may be intended to be ingested as contained in a food or drink for humans or in a drinking water or feed for animals.

The immunoadjuvant composition or vaccine composition of the present invention may be administered in a single dose, or in multiple doses at intervals of about 2 days to 8 weeks.

The dose of the vaccine may vary depending on the kind of a target allergy or infection, or on the animal species to which the vaccine is to be administered, but the single dose may be several dozen nanograms to several milligrams.

The single dose of the inhibitor may be about 1 µg/ml to 100 mg/ml. In cases where the immunoadjuvant composition or vaccine composition is combined with an immunoadjuvant other than the immunoadjuvant of the present invention, the single dose of the immunoadjuvant to be combined may be about 1 µg/ml to 100 mg/ml.

(IV) Vaccine Cell Preparation

The immunoadjuvant composition of the present invention is brought into contact with immune cells (for example, dendritic cells, lymphocytes, or the like) harvested from a subject, thereby activating the immune cells. In this way, activated immune cells can be obtained. The administration of the activated immune cells to a human is expected to bring about a vaccine effect, which activates the immunity. This activated immune cell preparation may be usually administered intravenously.

The harvested immune cells may be precultured in a medium such as RPMI in the presence of a cytokine. The immune cells are then mixed with the immunoadjuvant composition and incubated at a suitable temperature for cell growth, for example, at about 37° C. for about 1 to 24 hours.

The use ratio of the immune cells and the immunoadjuvant composition may be, for example, about 1:1 to 1:10000.

EXAMPLES

The reagents and test methods that were used in Examples are as follows.

<Reagents and Cells>

ELISA kits for mouse IL-4, IL-6, IL-12p40, IL-17, IFN-γ and TNF were purchased from R&D systems. A mouse ANA antibody (anti-nuclear antibody) ELISA kit was purchased. from Alpha Diagnostic. A monoclonal anti-YY1 (H-10) antibody and an HRP-conjugated monoclonal anti-β-tubulin (D-10) antibody were purchased from SantaCruz. An HRP-conjugated anti-FLAG antibody was purchased from Sigma. A TLR ligand including MALP-2, poly(I:C), a lipopolysaccharide (LPS) derived from *Salmonella Minnesota* Re595 strain, R-848, and a CpG oligonucleotide (ODN1668) were obtained as described in Kawagoe, T. et al. Sequential control of Toll-like receptor-dependent responses by IRAK1 and IRAK2. Nat Immunol 9, 684-91 (2008).

Peritoneal exudate cells were isolated from the peritoneal cavity of a mouse 3 days after injection with 2 ml of a 4.0% thioglycollate medium (Sigma) by washing with an ice-cold Hank's buffered salt solution (Invitrogen). A HEK 293 Tet-off cell line was purchased from Clontech. HEK 293 cells were purchased from ATCC.

<Expression Plasmid>

Zc3h12a cDNA (NCBI Accession No. NM__153159) was inserted into a pFLAG-CMV2 vector (Invitrogen) to give a Zc3h12a expression plasmid. A pFLAG-CMV2 vector (Invitrogen) was used as an empty control plasmid for the Zc3h12a expression plasmid. Point mutations (C306R or D141N) and deletion of the CCCH domain were carried out using the above Zc3h12a expression plasmid using QuickChange II Site-Directed Mutagenesis Kit (Stratagene) according to an attached instruction manual. A pGL3 vector containing a full-length (1-403) or partial (1-70, 58-173, or 172-403) IL-6 3'-UTR sequence was supplied by Dr. W. Zhao and Dr. K. Kirkwood (Zhao, W., et al. p38alpha stabilizes interleukin-6 mRNA via multiple AU-rich elements. J Biol Chem 283, 1778-85 (2008)). Parts (1-92, 1-102, 1-112, 1-132, 1-142, or 122-197) of IL-6 3'-UTR cDNA were separately inserted into a pGL3 vector according to the method described in Molecular Cloning: A Laboratory Manual, Cold Spring Harbor Laboratory Press. The 3'-UTR cDNA of β-globin (1-130) with or without IL-6 3'-UTR (77-108) sequence, the 3'-UTR cDNA of IL-12p40 (1-781), the 3'-UTR cDNA of CalcR (1-1601), and the 3'-UTR cDNA of interferon-γ (1-631) were separately inserted into a pGL3 vector according to the method described in Molecular Cloning: A Laboratory Manual, Cold Spring Harbor Laboratory Press. IL-6 CDS and IL-6 CDS+F3'-UTR were inserted into a pTREtight vector (Clontech) according to the method described in Molecular Cloning: A Laboratory Manual, Cold Spring Harbor Laboratory Press, to produce pTREtight-IL6-CDS and pTREtight-IL6-CDS+3'-UTR, respectively. A wild-type Zc3h12a cDNA and a mutant (D141N) Zc3h12a cDNA were inserted into a pGEX-6P1 vector (GE Healthcare) according to the method described in Molecular Cloning: A Laboratory Manual, Cold Spring Harbor Laboratory Press, to produce a pGEX-6P1-Zc3h12a plasmid and a Zc3h12a D141N mutant plasmid, respectively. IL-6 3'-UTR cDNA was inserted downstream of the T7 promoter in a pBluescript according to the method described in Molecular Cloning: A Laboratory Manual, Cold Spring Harbor Laboratory Press, to produce pBluescript-IL6 3'-UTR (1-430).

<ELISA>

IL-4, IL-6, IL-12p40, IL-17, IFN-γ, and TNF-α in culture supernatants, and a mouse ANA antibody in serum, were measured by ELISAs according to the manufacturer's protocol. ELISAs for mouse IgM, IgG1, IgG2a, IgG2b, IgG3, and an anti-double-stranded DNA antibody in serums were carried out according to the method described in Sato, S. et al. Essential function for the kinase TAK1 in innate and adaptive immune responses. Nat. Immunol 6, 1087-95 (2005); and Fukuyama, et al. The inhibitory Fcgamma receptor modulates autoimmunity by limiting the accumulation of immunoglobulin G+ anti-DNA plasma cells. Nat Immunol 6, 99-106 (2005).

<Northern Blotting, Immunoblotting, and EMSA>

Northern blotting, Immunoblotting and EMSA were carried out according to the methods described in Sato, S. et al. Essential function for the kinase TAK1 in innate and adaptive immune responses. Nat Immunol 6, 1087-95 (2005).

<Determination of Hematological Values>

Hematological analysis of blood samples prepared from wild-type and Zc3h12a$^{-/-}$ mice were performed at SRL Inc.

<Flow Cytometry>

Antibodies for flow cytometric analysis were purchased from BD. Cell suspensions of spleen were prepared by filtration and gentle pipetting. For surface staining, the cells were maintained in the dark at 4° C. The cells were washed with an ice-cooled FACS buffer (2% FCS, 0.02% NaN$_3$ in PBS) and incubated with each antibody for 15 minutes and washed 3 times with FACS buffer. FoxP3$^+$regulatory T cells were stained using Mouse Regulatory T Cell Staining Kit (eBioscience) according to the manufacturer's instructions. Intracellular cytokines were stained using BD Cytofix/Cytoparm Plus Fixation/Permeabilization Kit (BD) according to the manufacturer's instructions. Data were acquired on a FACS Calibur (registered trademark) or FACS Canto (registered trademark) II flow cytometer (BD), and analyzed using FlowJo (a software front Tree Star).

<Measurement of RNA Stability>

The stability of mRNA was determined using the following three independent methods.

(1) Stability of mRNA in Macrophages

Peritoneal macrophages (1×10$^6$) derived from wild-type and Zc3h12a$^{-/-}$ mice were separately stimulated with LPS (100 ng/ml) for 2 hours. Actinomycin D (2 µg/ml) was then added to the culture medium to stop transcription, and total RNAs were prepared after the indicated time periods. The RNAs were subjected to Northern blot analysis to determine IL-6, TNF, KC, and β-actin mRNA levels.

(2) Tet-Off System

HEK293 Tet-off cells (3×10$^6$) were transfected with pTREtight-IL6-CDS (having an IL-6 coding sequence) or pTREtight-IL6-CDS+3'-UTR (having an IL-6 coding sequence and non-coding 3'-UTR sequence), together with a wild-type Zc3h12a expression plasmid or a mutant Zc3h12a expression plasmid or an empty control plasmid. After 3 hours, the cells were subdivided into three 60-mm dishes and cultured overnight. mRNA transcription from the pTREtight vectors was terminated by addition of Dox (1 µg/ml), and total RNAs were prepared after the indicated time periods. The RNAs were subjected to Northern blot analysis to determine IL-6 and β-actin mRNA levels.

(3) Luciferase Assay

HEK293 cells were transfected with a pGL3-IL6-3'-UTR plasmid or a pGL3-empty plasmid, together with a Zc3h12a expression plasmid or an empty control plasmid. After 48 hours of cultivation, the cells were lysed and luciferase activities in the lysates were determined using Dual-Luciferase Reporter Assay System (Promega). The cells were simultaneously transfected with the *Renilla* luciferase gene as an internal control.

<In Vitro RNA Cleavage Assay>

Cleavage activities of wild-type and mutant forms of Zc3h12a were analyzed according to the method described in Miyoshi, K., et al. In vitro RNA cleavage assay for Argonaute-family proteins. Methods Mol Biol 442, 29-43 (2008). After incubation of a recombinant Zc3h12a protein with in vitro transcribed [$^{32}$P]-labeled RNA, the cleaved RNA was purified and analyzed by denaturing PAGE and autoradiography.

In particular, the recombinant protein and in vitro transcribed [$^{32}$P]-labeled RNA (5000 cpm) were mixed in cleavage buffer (25 mM Hepes, 50 mM KOAc, and 5 µM DTT) with or without 5 mM Mg (Oac)$_2$ in the presence of Rnasin plus (40 U) (Promega). The cleaved RNA was purified with TRIzol (Invitrogen) and analyzed by denaturing PAGE using 6% TBE-Urea gel (Invitrogen) and autoradiography.

<Bone Marrow Transplantation>

Bone marrow cells were separately prepared from a wild-type mouse and from the Zc3h12a$^{-/-}$ mouse. The prepared bone marrow cells were intravenously injected into a lethally irradiated CD45.1 C57BL/6 mouse (bred at Animal Resource Center for Infectious Diseases, Research Institute for Microbial Diseases, Osaka University). The chimeric mouse was given neomycin and ampicilin in its drinking water for 4 weeks. The mouse was analyzed at least 8 weeks after reconstitution. More than 90% of splenocytes from the chimeric mouse were CD45.2-positive.

<Expression of Zc3h12a Protein in Bacteria>

The protein was expressed in *Escherichia coli* BL21-Gold (DE3)pLysS (Stratagene) transformed with a pGEX-6P1-Zc3h12a or Zc3h12a (D141N) mutant plasmid. After expression of the protein, the cells were collected and resuspended in PBS. The cells were lysed by sonication followed by addition of Triton X-100 at a final concentration of 1% and incubation for 30 minutes at 4° C. with gentle shaking. The debris was then removed by centrifugation and the supernatant was incubated with Glutathione Sepharose 4B (GE Healthcare) for 30 minutes at 4° C. with gentle shaking. The resins were collected and washed 5 times with PBS and resuspended in PreScission Protease cleavage buffer (50 mM Tris, 150 mM NaCl, 1 mM EDTA and 1 µM DTT). PreScission Protease (GE Healthcare) (80 U) was added and incubated for 4 hours at 4° C. with gentle shaking. The supernatant was collected and stored at −80° C. as a recombinant protein solution.

<Synthesis of [$^{32}$P]-labeled RNA>

The pBluescript-IL6 3'-UTR (1-430) plasmid was used as a template for the synthesis of RNA having an IL6 3'-UTR sequence. In vitro RNA synthesis and [$^{32}$P]-labeling were performed using Riboprobe in vitro Transcription system (Promega) according to manufacturer's instructions. The 5'-end labeling was performed using non-labeled RNA and Kinase Max 5'-end labeling Kit (Ambion) according to the manufacturer's instructions. The 3'-end labeling was performed by incubation of non-labeled RNA with T4 RNA Ligase (Takara) and [$^{32}$P]pCp (GE Healthcare).

<RNA Binding Assay>

[$^{32}$P]-labeled RNA (1×10$^6$ cpm) was mixed with the recombinant protein or BSA (Pierce) in a buffer (25 mM Hepes, 50 mM KOAc, and 5 µM DTT) and incubated for 20 minutes at room temperature. Heparin was then added at a final concentration of 5 µg/ml and incubated for further 10 minutes. The sample was cross-linked by irradiation with 254-nm ultraviolet light using FUNA-UV-LINKER FS-800 (Funakoshi) at a distance of 5 cm from the light source for 20 minutes on ice. The cross-linked sample was treated with RNaseT (100 U) for 20 minutes at room temperature, followed by treatment with RNaseA (1 µg) for 15 minutes at 37° C. After the digestion, the protein bound with [$^{32}$P]-labeled RNA was analyzed by SDS-PAGE and autoradiography.

<Microarray Analysis>

Peritoneal macrophages from a wild-type mouse (purchased from CLEA Japan), a MyD88$^{-/-}$ mouse (produced by the method described in Adachi O, Kawai T, Takeda K, Matsumoto M, Tsutsui H, Sakagami M, Nakanishi K, Akira S. Targeted disruption of the MyD88 gene results in loss of IL-1- and IL-18-mediated function. Immunity. 1998 July; 9(1): 143-50.), and a Trif$^{-/-}$ mouse (produced by the method described in Yamamoto M, Sato S. Hemmi H, Hoshino K, Kaisho T, Sanjo H, Takeuchi O, Sugiyama M, Okabe M, Takeda K, Akira S. Role of adaptor TRIF in the MyD88-independent toll-like receptor signaling pathway. Science. 2003 Aug. 1; 301(5633): 640-3) were stimulated with 100 ng/ml LPS for 0, 1 and 4 hours. Total RNA was extracted with RNeasy kit (Qiagen, Hilden, Germany), and double-stranded cDNA was synthesized from 10 µg of the total RNA with SuperScript Choice System (Invitrogen, Carlsbad, Calif.) primed with T7-(dT) 24 primer. The cDNA was used to prepare biotin-labeled cRNA by an in vitro transcription reaction performed using T7 RNA polymerase in the presence of a biotinylated ribonucleotide, according to the manufacturer's protocol (Enzo Diagnostics, Farmingdale, N.Y.). The cRNA product was purified using an RNeasy kit (Qiagen), fragmented, and hybridized to Affymetrix mouse expression array A430 microarray chip (Affymetrix, Santa Clara, Calif.) according to the manufacturer's protocol. For determination of a LPS-inducible gene in Zc3h12a$^{-/-}$ macrophages, peritoneal macrophages were stimulated with 100 ng/ml LPS. Total RNA was then extracted with TRIzol (Invitrogen Life Technologies) and further purified using an RNeasy kit. Biotin-labeled cDNA was synthesized from 100 ng of the purified RNA using Ovation Biotin RNA Amplification and Labeling System (Nugen) according to the manufacturer's protocol. Hybridization, staining, washing and scanning of Affymetrix mouse Genome 430 2.0 microarray chip were done according to the manufacturer's instructions. Robust multichip average (RMA) expression values were calculated using R and Bioconductor affy package. For hierarchical clustering, probes having a more than two- or fivefold increased RMA expression value compared to that at 0 hours after stimulation were selected. The RNA expression values were transformed to fit averages and standard deviations to zero and one by each probe. For analysis of LPS-inducible genes in MyD88$^{-/-}$ and Trif$^{-/-}$ macrophages, distances between probes were calculated using Pearson's correlation coefficient as a distance function. For analysis of LPS inducible genes in Zc3h12a$^{-/-}$ macrophages, principle component analysis for RMA values was performed and Euclidean distances between probes were computed using the first to the fifth principle components. Hierarchical clustering was carried out using these distances with Ward's method. These calculations and generation of heat map representation were carried out using R and Bioconductor.

<Immunohistochemistry Analysis>

Tissues were fixed with a 10% formalin neutral buffer solution, embedded in paraffin, and cut into 5-µm thick sections. The sections were heated in Target Retrieval Solution (Dako, Glostrup, Denmark) at 98° C. for 40 minutes to facilitate antigen retrieval. The sections were incubated with peroxidase-conjugated goat IgG fraction to mouse IgA (α chain) (MP Biomedicals, LLC, Solon, Ohio) diluted 1:50 with an antibody diluent (product name: ChemMate Dako), or peroxidase-conjugated goat affinity purified F(AB')₂ fragment to mouse IgG (whole molecule) (MP Biomedicals) diluted 1:25 with an antibody diluent, for 30 minutes at room temperature. Immunoreacted cells for mouse IgA and IgG were visualized with diaminobenzidine (Dako). The sections were lightly counterstained with haematoxylin. The stained sections were observed under an optical microscope.

<Structure Modeling>

A model of the Zc3h12c N-terminal domain was constructed as follows.

First, the sequence was submitted to the BioInfoBank Meta Server (http://bioinfo.pl), and the top ten models were built using default settings. The best model was then chosen by submitting each to the SeSAW functional annotation server (http//pdbjs6.pdbj.org/SeSAW/), and selecting the model with the highest score. The model chosen was built from a structural genomics template 2qip using the FFAS03 server (http://ffas.1jcrf.edu/ffas-cgi/cgi/ffas.pl) and Modeller (Eswar, N. et al. Comparative protein structure modeling using Modeller. Curr Protoc Bioinformatics Chapter 5, Unit 5.6 (2006)). This model, which also had the highest 3D Jury score, contained a cluster of conserved aspartic acids (D141, D226, S242, D244 and D248) that are also conserved in the active sites of Flap endonucleases (for example, PDB ID lut5) (Feng, M. et al. Roles of divalent metal ions in flap endonuclease-substrate interactions. Nat Struct Mol Biol 11, 450-6 (2004)). Electrostatic surfaces were prepared using the eF-surf server (http://ef-site.hgc.jp/eF-surf/) and eF-site (Kinoshita, K. & Nakamura, H. eF-site and PDBjViewer: database and viewer for protein functional sites. Bioinformatics 20, 1329-30 (2004)).

Example 1

Identification of Zc3h12a as LPS-Inducible Gene

To examine Toll-like receptor (TLR) induced gene expression comprehensively, the inventors performed microarray analysis using mouse macrophages from wild-type (WT), Myd88$^{-/-}$, and Trif$^{-/-}$ mice stimulated with LPS.

214 genes of which expression was induced twofold or more 1 or 4 hours after stimulation in wild-type cells were selected. Hierarchical clustering of these LPS-inducible genes showed that they could be classified into three major clusters (data not shown). Among the clusters, genes in Cluster III were rapidly induced in a MyD88-dependent manner. This cluster contained, among others, Tnf, Nfkbiz and Zfp36. Cluster III also contained the gene encoding Zc3h12a (data not shown).

To investigate the expression of Zc3h12a, IL-6, IκBζ, and β-actin, total RNA from macrophages stimulated with LPS (100 ng/ml) for the indicated time periods was extracted and subjected to Northern blot. The results are shown in FIG. 1a. Northern blot analysis confirmed that Zc3h12a mRNA was rapidly induced in mouse macrophages after LPS stimulation and then gradually decreased with time (FIG. 1a). Zc3h12a has a CCCH-type zinc-finger (Zf) motif, and forms a family with the homologous proteins Zc3h12b, Zc3h12c and Zc3h12d.

HEK293 cells were transfected with or without Flag-tagged Zc3h12a using Lipofectamine 2000 (Invitrogen). Cytoplasm (CP) and nuclear extracts (NE) were prepared from the HEK293 cells transfected with or without Flag-tagged Zc3h12a. The expression of Zc3h12a was measured by Western blotting using an anti-FLAG antibody. An anti-β-tubulin antibody and an anti-YY-1 antibody were used as controls (loading controls) of CP and NE, respectively. The results are shown in FIG. 1b. The fractionation experiments showed that the Zc3h12a protein is mainly localized in the cytoplasm, rather than in the nucleus (FIG. 1b).

Example 2

Generation of Zc3h12a$^{-/-}$ Mouse

To investigate the functional roles of Zc3h12a in the control of immune responses in vivo, the inventors generated a Zc3h12a-deficient (Zc3h12a$^{-/-}$) mouse.

Genomic DNA containing Zc3h12a was isolated from GSI-I embryonic stem cells by PCR using Elongase (Invitrogen). The isolated genomic DNA containing Zc3h12a was characterized by restriction enzyme mapping and sequencing analysis. A targeting vector was designed to replace exon 3 to exon 5 containing the CCCH type zinc-finger domain, with a neomycin-resistance gene. A 1.1-kilobase (kb) ClaI-BamI fragment was used as the 3' homology region, and a 5.9-kb NotI-SalI fragment was used as the 5' homology region. A total of 30 μg of NotI-linearized vector was electroporated into GSI-I embryonic stem cells. After selection with G418 (Nacalai Tesque), drug-resistant clones were picked up and screened by PCR and Southern blot analysis. These clones were individually microinjected into blastocysts derived from a C57BL/6 mouse (purchased from CLEA Japan), and the blastocysts were transplanted to a pseudopregnant female mouse. Matings of a chimeric male mouse to a C57BL/6 female mouse resulted in the transmission of the mutant allele to the germ line. Resulting Zc3h12a$^{+/-}$ mice were intercrossed to generate a Zc3h12a$^{-/-}$ mouse. All animal experiments were done with the approval of the Animal Research Committee of the Research Institute for Microbial Diseases, Osaka University.

Figure 2:
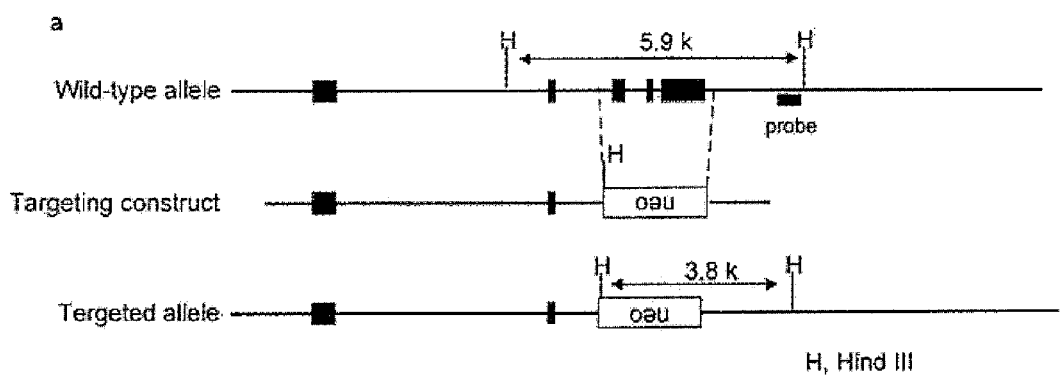
FIG. 2a is schematic views of a mouse Zc3h12a gene (wild-type allele), a targeting vector (targeting construct), and a target allele.
FIG. 2b is the results of Southern blot analysis in heterozygous cross progeny.
FIG. 2c is the results of RT-PCR analysis of RNAs from wild-type (WT) and Zc3h12a$^{-/-}$ macrophages stimulated with LPS.
Figure 2:

FIG. 2a is schematic views of a mouse Zc3h12a gene (wild-type allele), a targeting vector (targeting construct), and a target allele. In FIG. 2a, H represents HindIII. FIG. 2b is the results of Southern blot analysis in heterozygous cross progeny. Genomic DNA was extracted from mouse embryo fibroblasts (MEF), cleaved with HindIII, separated by electrophoresis, and hybridized with a radioactively labeled probe. Southern blotting showed a single band of 5.9 kb for a wild-type ($^{+/+}$) mouse, a single band of 3.8 kb for a homozygous-type ($^{-/-}$) mouse, and both bands of 5.9 kb and 3.8 kb for a heterozygous-type ($^{+/-}$) mouse.

To investigate the expression of Zc3h12a mRNA, the inventors subjected RNA to RT-PCR analysis using the two kinds of primers shown in FIG. 2a, Fw: ATATGAGTGAC-CCTTGTGGAACGAAGC (SEQ ID: NO. 1) and Rev: TCT-GTACACAGCATACATGTGTCCTCC (SEQ ID: NO. 2). The expression of the β-actin gene was analyzed using the same RNA.

FIG. 2c shows the results of RT-PCR analysis of RNAs from wild-type (WT)(Zc3h12a$^{+/+}$) and Zc3h12a$^{-/-}$ macrophages stimulated with LPS (100 ng/ml) for the indicated time periods. The RT-PCR analysis revealed that the expression of Zc3h12a is inhibited in Zc3h12a$^{-/-}$ macrophages (FIG. 2c).

Example 3

Early Onset of Fetal Autoimmune Disease in Zc3h12a$^{-/-}$ Mice

Figure 3:
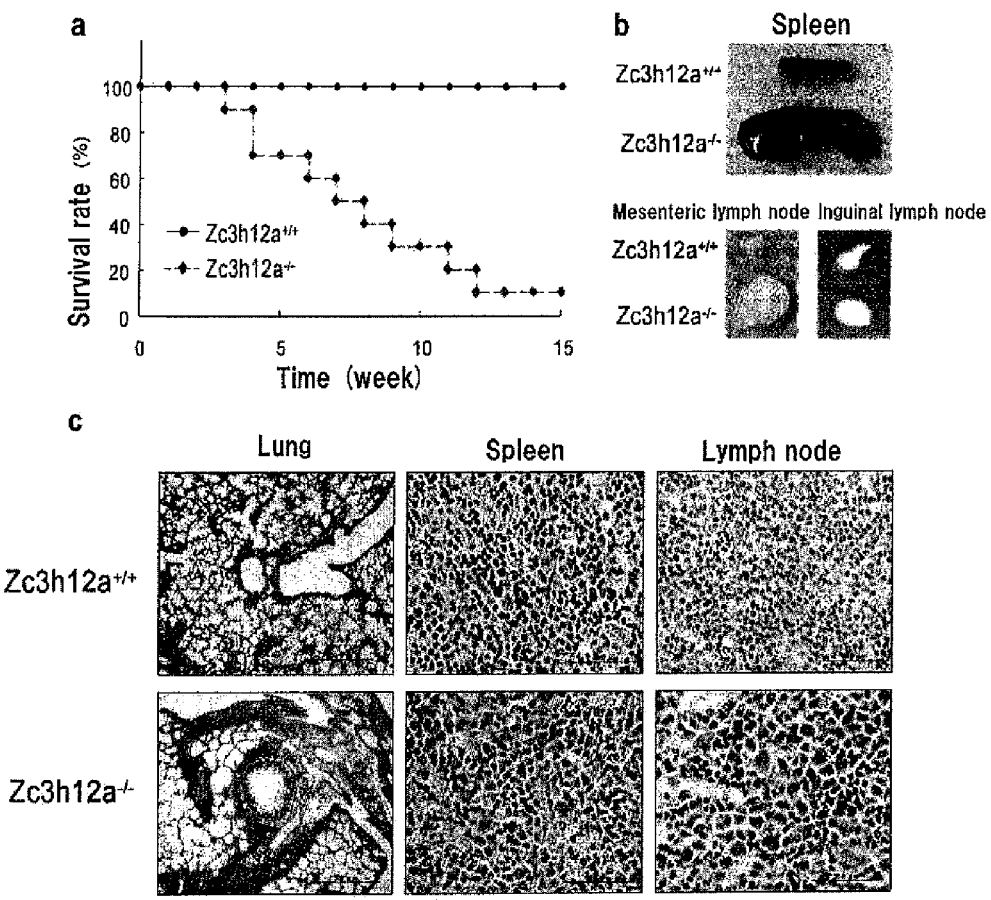
FIG. 3a is a graph showing the survival rates of wild-type (Zc3h12a$^{+/+}$) and Zc3h12a$^{-/-}$ mice.
FIG. 3b is the photographs of spleens (top), mesenteric lymph nodes (bottom left), and inguinal lymph nodes (bottom right) from wild-type and Zc3h12a$^{-/-}$ mice.
FIG. 3c is the histological photographs of lungs, spleens and lymph nodes from wild-type and Zc3h12a$^{-/-}$ mice.
Figure 4:
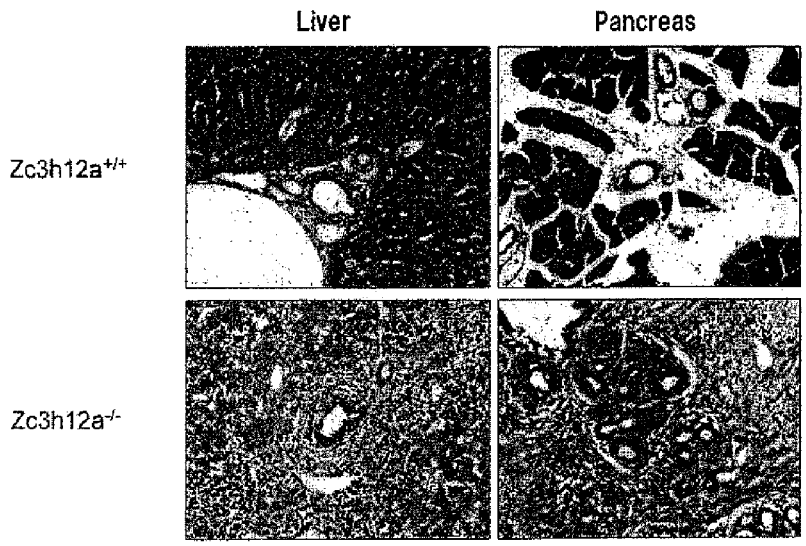
FIG. 4 is the histological photographs of liver and pancreas sections from wild-type (WT) and Zc3h12a$^{-/-}$ mice.

Zc3h12a$^{-/-}$ mice are born according to Mendel's law. Most of them showed growth retardation and spontaneously died within 12 weeks of birth (FIG. 3a). FIG. 3a is a graph showing the survival rates of wild-type (Zc3h12a$^{+/+}$) and Zc3h12a$^{-/-}$ mice (n=10). FIG. 3b is the photographs of spleens (top), mesenteric lymph nodes (bottom left) and inguinal lymph nodes (bottom right) from wild-type (Zc3h12a$^{+/+}$) (top) and Zc3h12a$^{-/-}$ (bottom) mice. Zc3h12a$^{-/-}$ mice showed severe splenomegaly and lymphoadenopathy (FIG. 3b). FIG. 3c is the histological photographs of the lungs, spleens and lymph nodes (LN) from wild-type (Zc3h12a$^{+/+}$) and Zc3h12a$^{-/-}$ mice. FIG. 4 is the results of H&E staining of liver and pancreas sections from wild-type (WT) and Zc3h12a$^{-/-}$ mice. The histological examination revealed infiltration of plasma cells in the lung, paraepithelium of the bile duct and spleen (FIGS. 3c and 4). Plasma cells also accumulated in Zc3h12a$^{-/-}$ lymph nodes (LN) and spleen (FIG. 3c). In the LN, granuloma formation and the generation of giant cells with fused macrophages were observed. Nevertheless, inflammatory changes were not observed in either the intestine or the joints of Zc3h12d$^{-/-}$ mice (data not shown).

The examination results of blood cells are shown in Table 1. Zc3h12a$^{-/-}$ mice showed an increase in the numbers of white blood cells and platelets and suffered from severe anemia (Table 1). Data in Table 1 are the mean±the standard deviation (S.D.) of six samples.

TABLE 1

|  | Zc3h12a$^{+/+}$ | Zc3h12a$^{-/-}$ |
| --- | --- | --- |
| Platelet (×10$^4$ mm$^{-3}$) | 62.7 ± 18.9 | 134.1 ± 27.9 |
| White blood cell (μl$^{-1}$) | 2083.3 ± 652.4 | 6833.3 ± 2309.7 |
| Red blood cell (×10 mm$^{-3}$) | 841.7 ± 30.0 | 450.7 ± 89.5 |
| Hemoglobin (g/dl$^{-1}$) | 14.7 ± 0.4 | 6.1 ± 1.5 |
| Hematocrit (%) | 49.9 ± 1.5 | 26.1 ± 3.8 |
| MCV (μ$^3$) | 59.3 ± 1.2 | 58.5 ± 3.9 |
| MCH (pg) | 17.5 ± 0.5 | 13.5 ± 1.5 |
| MCHC (%) | 29.3 ± 0.5 | 23.2 ± 3.0 |

Figure 5:
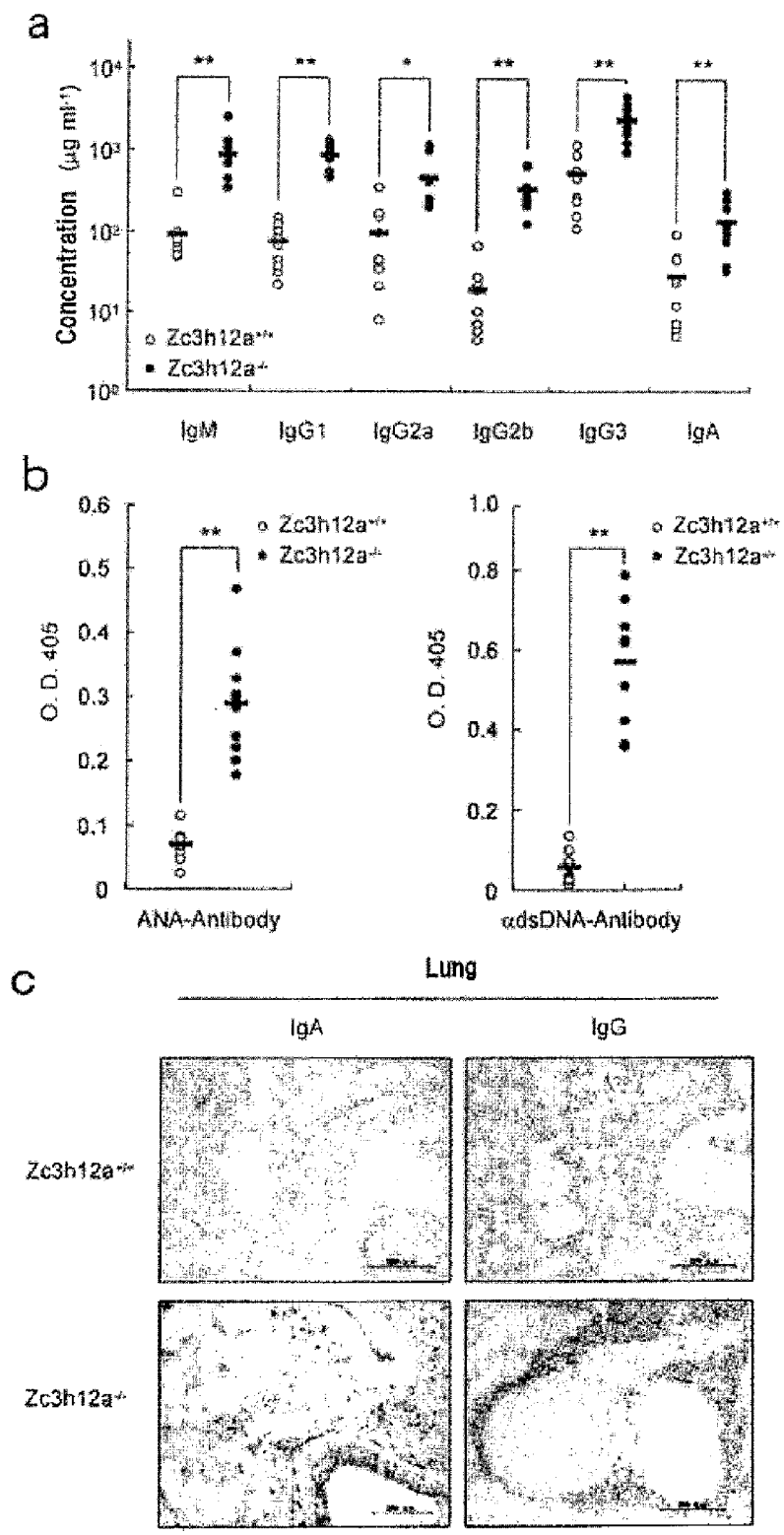
FIG. 5 is a graph showing serum immunoglobulin levels (a), the measurement results of production of an antinuclear antibody and an anti-double stranded DNA antibody (b), and the results of histological examinations (c) in Zc3h12a$^{-/-}$ mice.

Furthermore, Zc3h12a$^{-/-}$ mice developed hyperimmunoglobulinemia (hyperyglobulinemia) of all immunoglobulin isotypes tested (FIG. 5a). Serum immunoglobulin levels in Zc3h12a$^{-/-}$ mice are shown in FIG. 5a.

Production of an anti-nuclear antibody (ANA) and an anti-double-stranded DNA antibody in Zc3h12a$^{-/-}$ mice is shown in FIG. 5b. Statistical significance was determined using the Student's t-test (*: P<0.05, **: P<0.01). Production of an anti-nuclear antibody and an anti-double-stranded DNA antibody was observed in Zc3h12a$^{-/-}$ mice (FIG. 5b).

FIG. 5c is the immunohistochemical results (histological photographs) of lung sections stained with anti-IgG and anti-IgA antibodies. Plasma cells infiltrated in the lung interstitial tissues were readily stained with anti-IgG or anti-IgA antibodies (FIG. 5c).

Figure 6:
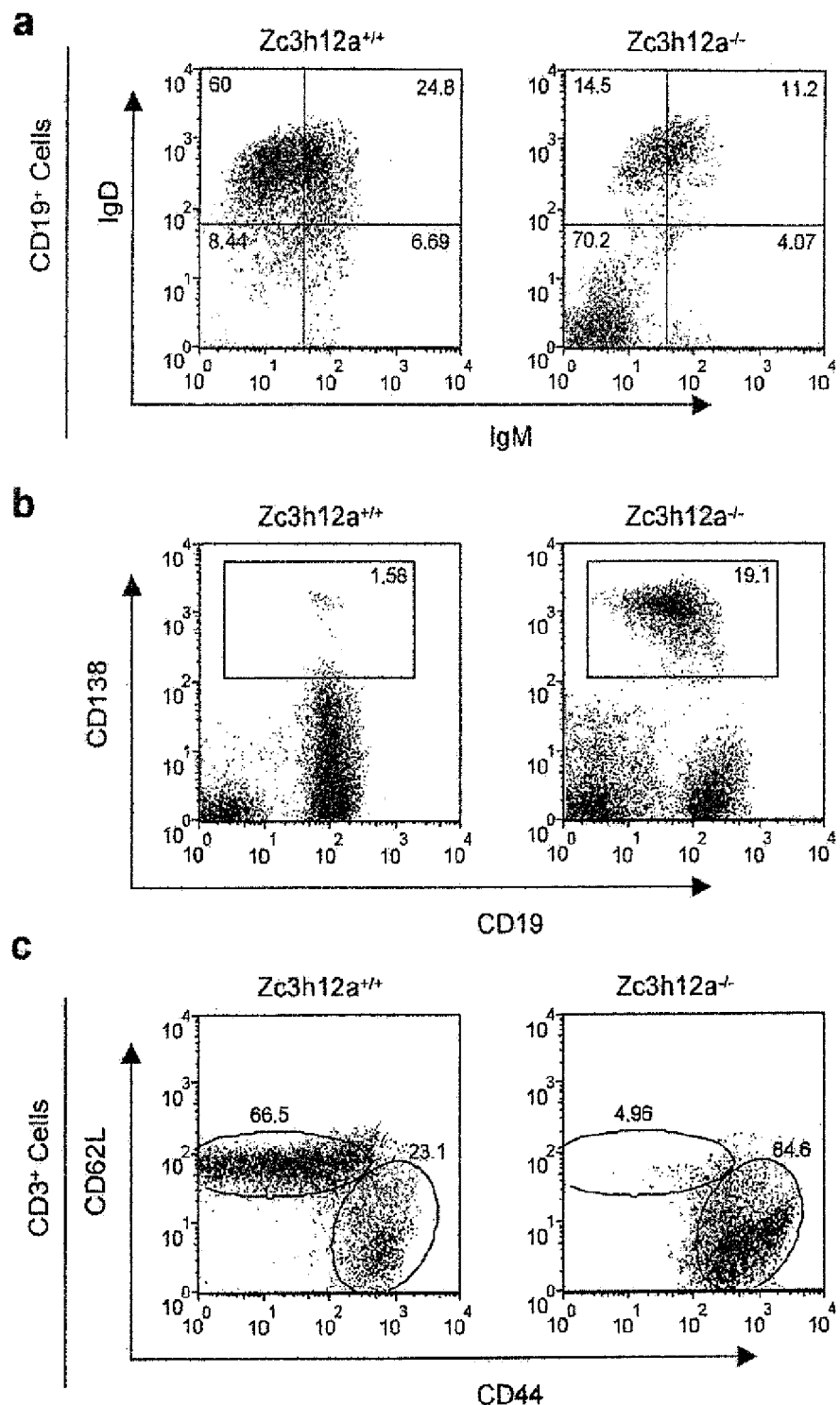
FIG. 6 is graphs showing the results of flow cytometric analysis of antibody-stained splenocytes from Zc3h12a$^{-/-}$ mice.

FIG. 6 shows the examination results of cellular abnormalities and augmented cytokine production in Zc3h12a$^{-/-}$ mice. FIGS. 6a to 6c show flow cytometric analysis of splenocytes. The expression of IgM and IgD in splenic CD19$^+$ B cells is shown in FIG. 6a, the proportion of plasma cells in the spleen is shown in FIG. 6b, and the expression of CD62L and CD44 in splenic T cells is shown in FIG. 6c. About the above results, similar results were obtained in three independent experiments.

Figure 7:
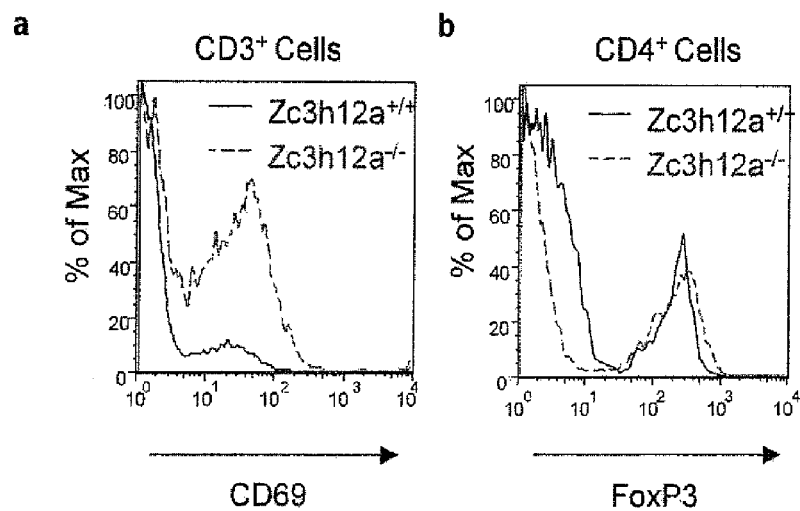
FIG. 7 is graphs showing the results of flow cytometric analysis of antibody-stained mouse splenocytes.

FIG. 7a is a graph showing the results of flow cytometric analysis of antibody-stained splenocytes from wild-type and Zc3h12a$^{-/-}$ mice. FIG. 7b is a graph showing the results of flow cytometric analysis of splenocytes stained with an anti-Foxp3 antibody and an anti-CD4 antibody.

Figure 8:
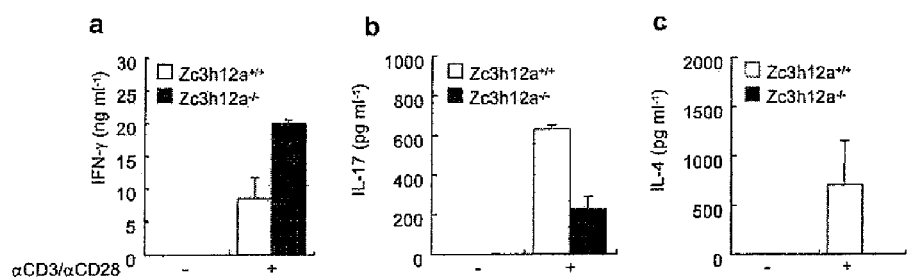
FIG. 8 is graphs showing production of interferon-γ (a), IL-17 (b), and IL-4 (c) in response to CD3/CD28 stimulation in splenic T cells.

FIG. 8 is graphs showing production of interferon-γ, IL-17, and IL-4 in response to CD3/CD28 stimulation in splenic T cells. Error bars indicate the standard deviation (S.D.) of duplicates. Similar results were obtained in three independent experiments.

Figure 9:
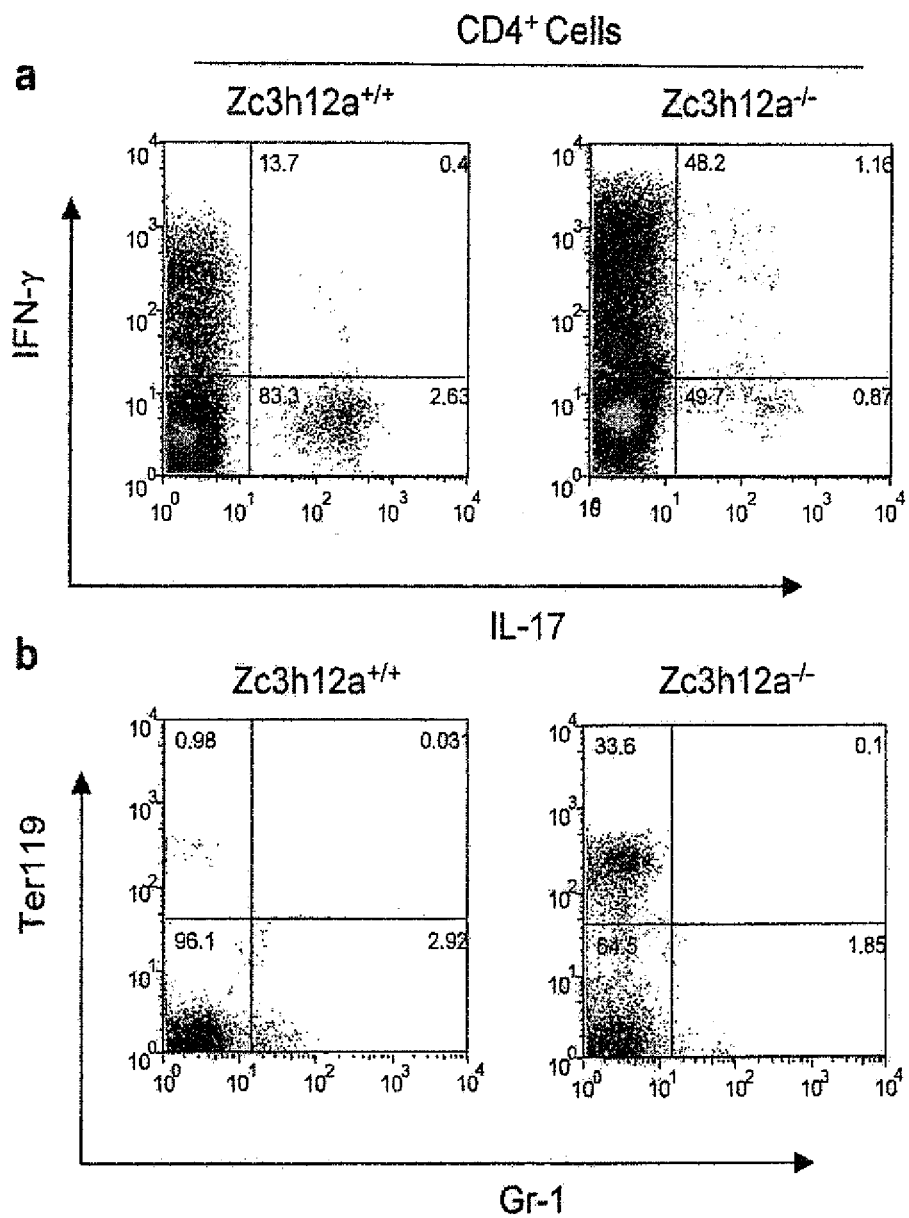
FIG. 9 is graphs showing the results of flow cytometric analysis of antibody-stained mouse splenocytes.

FIG. 9a is the results of flow cytometric analysis of splenocytes stained with an anti-CD4 antibody, permeated, and stained for interferon-γ and IL-17. Splenocytes were stimulated by incubation with 50 ng/ml phorbol myristate acetate (PMA) (Sigma), 5 mM calcium ionophore A23187 (Sigma), and Golgistop (BD) in a complete medium for 4 hours at 37° C., and the stimulated splenocytes were used for the above analysis. The numbers in the Figure indicates the proportion of the cells in a quadrant.

Figure 10:
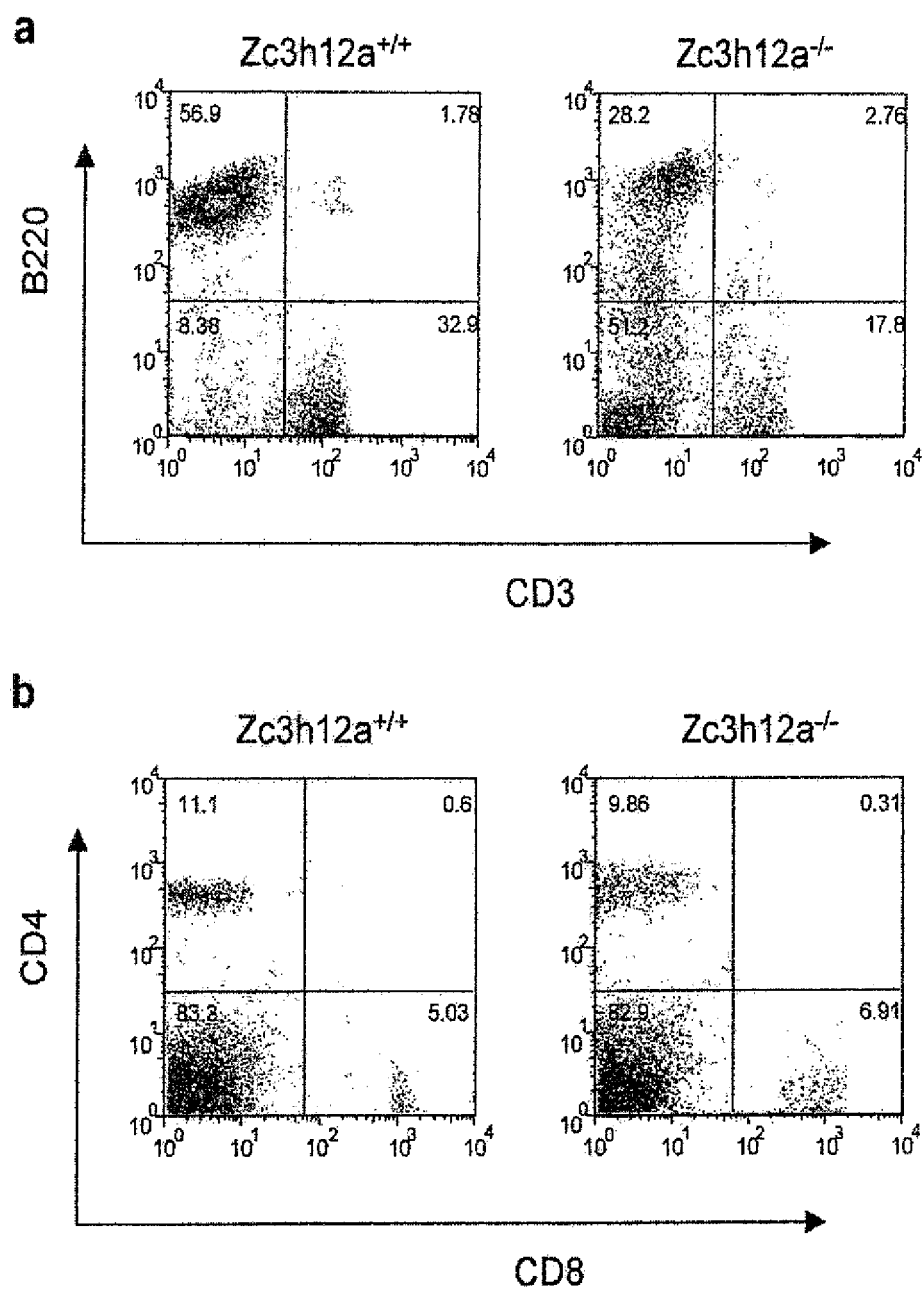
FIG. 10 is graphs showing the results of flow cytometric analysis of antibody-stained mouse splenocytes.

FIGS. 9b, 10a, and 10b are graphs showing the results of flow cytometric analysis of antibody-stained splenocytes from wild-type and Zc3h12a$^{-/-}$ mice.

Figure 11:
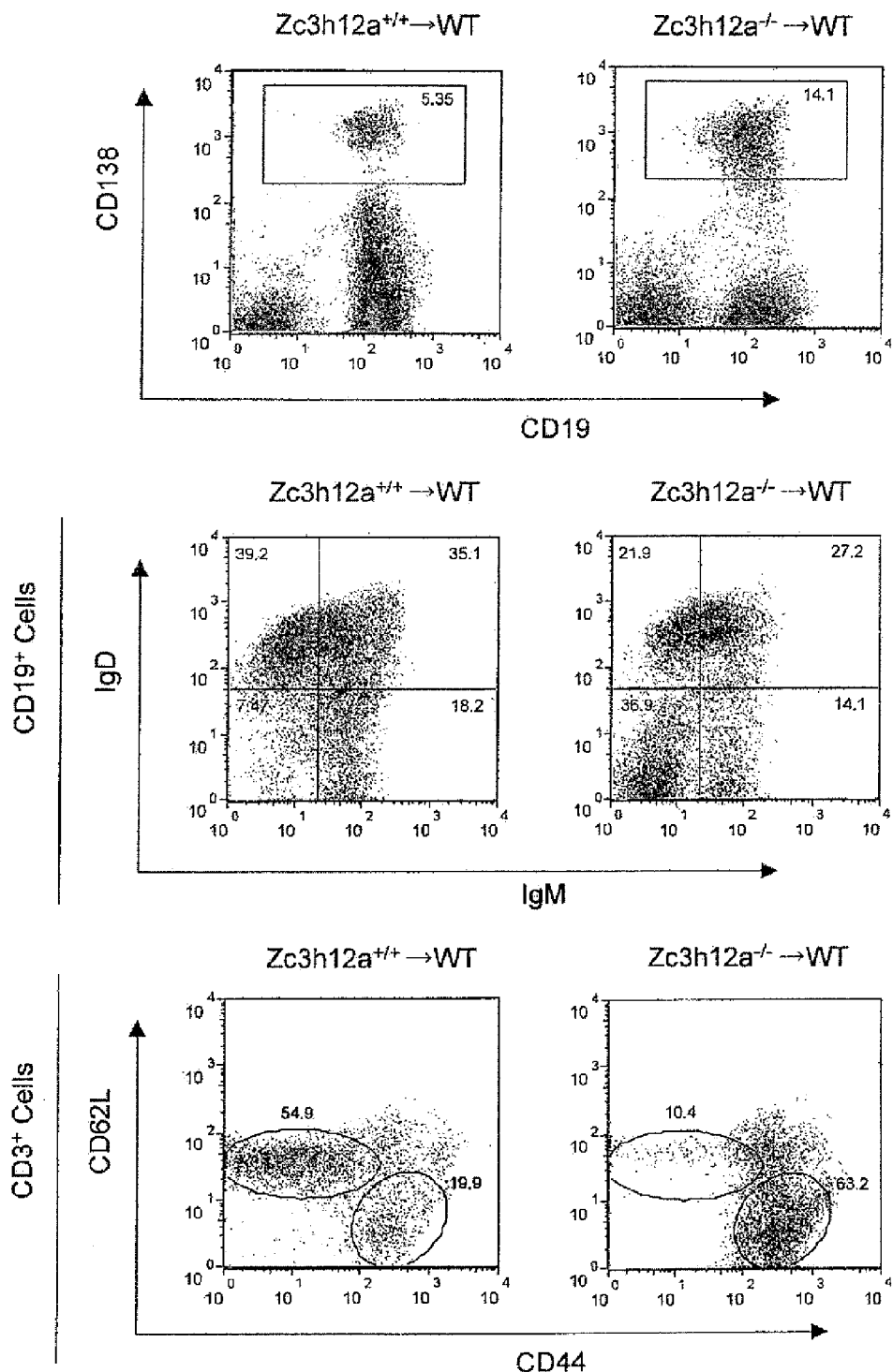
FIG. 11 is graphs showing the results of flow cytometric analysis of antibody-stained splenocytes from wild-type and Zc3h12a$^{-/-}$ bone marrow chimeric mice.

FIG. 11 is the examination results of the involvement of hematopoietic cells in the accumulation of plasma cells and effector/immunological memory T cells in Zc3h12a$^{-/-}$ mice. In the experiment shown in FIG. 11, splenocytes from wild-type and Zc3h12a$^{-/-}$ bone marrow chimeric mice were stained with antibodies and analyzed by flow cytometry.

The flow cytometric analysis showed that about 70% of CD19$^+$ B cells were IgM$^-$IgD$^-$, but not Ig$^+$, indicating that most Zc3h12a$^{-/-}$ mouse B cells underwent a class switch in the spleen (FIG. 6a). Furthermore, CD138$^+$CD19$^{dull}$ plasma cells were abundant in the Zc3h12a$^{-/-}$ mouse spleen (FIG. 6b). In addition, the expression of CD69 was upregulated in splenic CD3$^+$ T cells, and CD44$^{high}$CD62L$^-$ T cells accumulated in the periphery (FIGS. 6c and 7a). Nevertheless, the proportion of CD4Foxp3$^+$ regulatory T cells was comparable between wild-type and Zc3h12a$^{-/-}$ mice (FIG. 7b). Stimulation of splenic T cells with an anti-CD3 antibody resulted in increased production of IFN-γ, but not IL-17 (FIGS. 8 and 9a). A Ter119$^+$ erythroblast population was higher in the Zc3h12a$^{-/-}$ mouse spleen, probably reflecting the responses to anemia (FIG. 9b).

However, the ratios of B cells to T cells and of CD4$^+$ cells to CD8$^+$ cells were not altered in the Zc3h12a$^{-/-}$ spleen (FIGS. 10a and 10b). To examine whether hematopoietic cells are sufficient for the development of disease, the inventors transplanted bone marrow cells from the Zc3h12a$^{-/-}$ mouse to a recipient C57BL/6 mouse. A Zc3h12a$^{-/-}$ BM chimera showed delayed, but marked, development of lymphadenopathy and accumulation of plasma cells and CD44$^{high}$CD62L$^+$ T cells, indicating that hematopoietic cells contribute to the development of immune disorders (FIG. 11).

These results demonstrate that Zc3h12a is essential for preventing the development of severe immune diseases characterized by Ig-producing plasma cells and the formation of granulomas.

Example 4

The inventors then examined cytokine production from macrophages.

Figure 12:
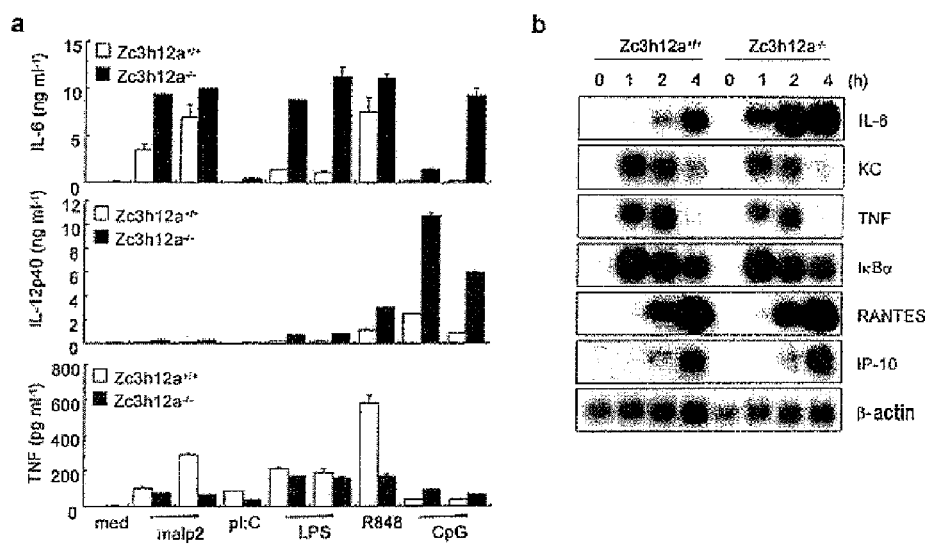
FIG. 12a is graphs showing the concentrations of IL-6, IL-12p40, and TNF derived from stimulated peritoneal macrophages, measured by ELISA.
FIG. 12b is the results of Northern blot analysis for the expression of IL-6, KC, TNF, IκBα, RANTES, IP-10 and β-actin, using RNAs derived from LPS-stimulated macrophages.

Peritoneal macrophages from wild-type and Zc3h12a$^{-/-}$ mice were stimulated with MALP-2 (1, 10 ng/ml), poly(I:C) (100 μg/ml), LPS (10, 100 ng/ml), R-848 (10 nM), or CpG-DNA (0.1, 1 μM) for 24 hours. The concentrations of IL-6, IL-12p40 and TNF in the culture supernatants were measured by ELISAs. The results are shown in FIG. 12a. In FIG. 12a, "med" denotes macrophages not stimulated by the above substances (control). Error bars indicate the standard deviation (S.D.) of duplicates. Similar results were obtained in three independent experiments.

Total RNA from macrophages stimulated with LPS (100 ng/ml) for the indicated time periods was extracted and subjected to Northern blotting for the expression of IL-6, KC, TNF, IκBα, RANTES, IP-10, and β-actin. The results are shown in FIG. 12b.

Figure 13:
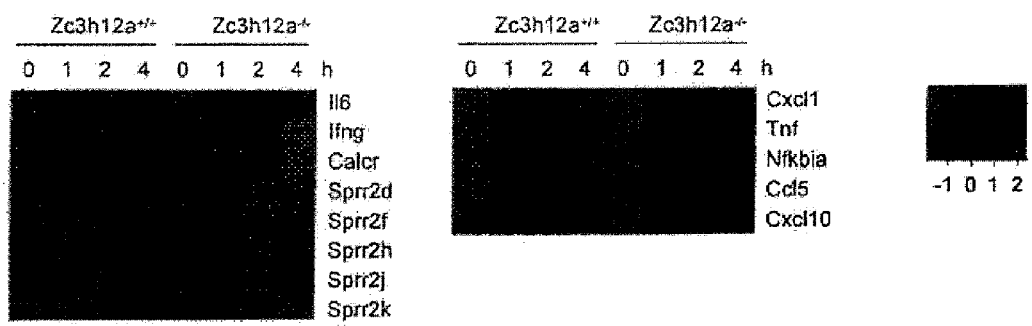
FIG. 13 is heat map representation of the expression of LPS-inducible genes selected on the basis of microarray analysis of wild-type and Zc3h12a$^{-/-}$ peritoneal macrophages.

FIG. 13 is heat map representation of the expression of LPS-inducible genes selected on the basis of microarray analysis of wild-type (Zc3h12a$^{+/+}$) and Zc3h12a$^{-/-}$ peritoneal macrophages.

Figure 14:
FIG. 14 is heat map representation and a dendrogram resulting from microarray analysis of LPS-inducible genes in wild-type and Zc3h12a$^{-/-}$ macrophages.

The inventors then performed microarray analysis of LPS-inducible genes in wild-type and Zc3h12a$^{-/-}$ macrophages. As described above, wild-type and Zc3h12a$^{-/-}$ macrophages were stimulated with 100 ng/ml LPS for 0, 1, 2, and 4 hours and total RNA was subjected to microarray analysis using Affymetrix mouse Genome 430 2.0 microarray chips. Data were processed as described above, 1045 genes upregulated 5 times or more in wild-type or Zc3h12a$^{-/-}$ macrophages 1, 2, or 4 hours after stimulation were defined as LPS-inducible genes. The genes were hierarchically clustered and a resulting heat map and dendrogram are shown in FIG. 14. In FIG. 14, a highly expressed gene cluster in Zc3h12a$^{-/-}$ macrophages is emphasized by a red rectangular frame.

Figure 15:
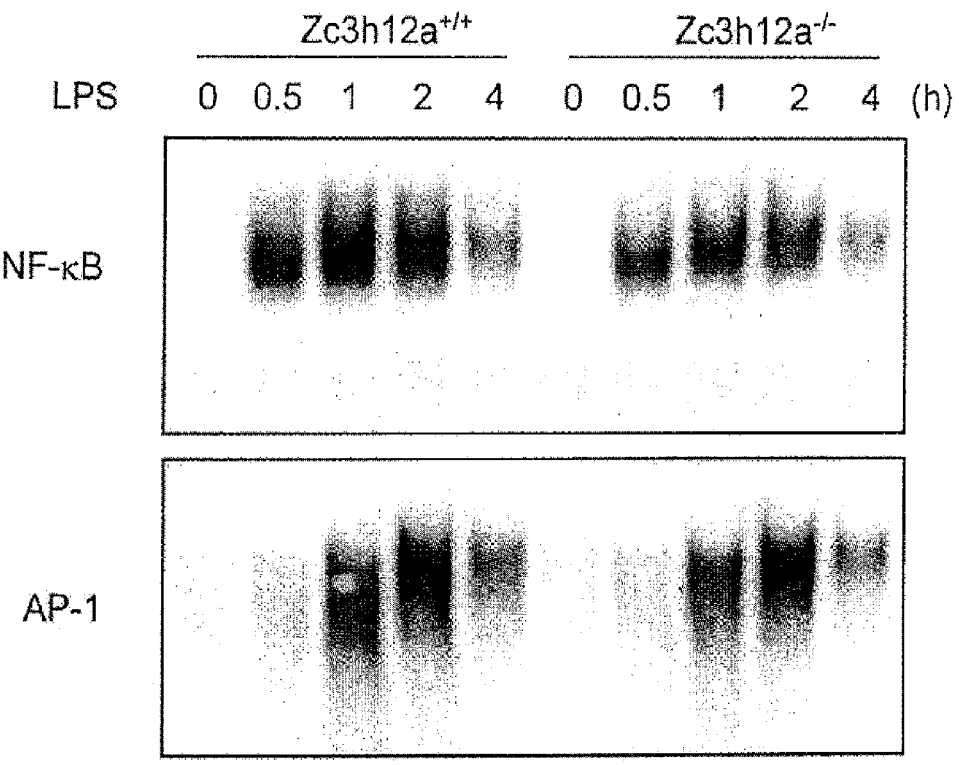
FIG. 15 is the results of electrophoretic mobility shift assay (EMSA) for transcription factor-DNA binding activity in the nuclear extracts of Zc3h12a$^{-/-}$ macrophages stimulated with LPS.

The inventors investigated whether the activation of TLR signaling pathways is normal in Zc3h12a$^{-/-}$ macrophages. Wild-type and Zc3h12a$^{-/-}$ macrophages were stimulated with LPS (100 ng/ml) for the indicated time periods. A nuclear extract was prepared and transcription factor-DNA binding activity was measured by electrophoretic mobility shift assay (EMSA) using specific probes for NF-κB and AP-1 (described in Sato, S. et al. Essential function for the kinase TAK1 in innate and adaptive immune responses. Nat Immunol 6, 1087-95 (2005)). The results are shown in FIG. 15. The results shown in FIG. 15 are typical for the three independent experiments.

As shown in FIG. 12a, the stimulation with TLR ligands, MALP-2 (TLR2), poly(I:C) (TLR3), LPS (TLR4), R-848 (TLR7) and CpG-DNA (TLR9) induced increased production of IL-6 and IL-12p40, but not of TNF, in Zc3h12a$^{-/-}$ macrophages. The Northern blot analysis showed that IL-6 mRNA, but not TNF, KC or IκNα mRNA, increased significantly in response to LPS in Zc3h12a$^{-/-}$ macrophages (FIG. 12b). The inventors then performed microarray analysis to assess the differences in LPS-inducible gene expression between wild-type and Zc3h12a$^{-/-}$ macrophages. The microarray analysis of LPS-inducible genes in macrophages showed that most LPS-inducible genes were comparably expressed in wild-type and Zc3h12a$^{-/-}$ cells (FIG. 14). Nevertheless, a particular set of genes was highly expressed in Zc3h12a$^{-/-}$ macrophages. These included IL-6, Ifng, Calcr and Sprr2d (FIG. 13). No differences were observed in the activation of NF-κB or the activator protein 1 (AP-1) by LPS between wild-type and Zc3h12a$^{-/-}$ macrophages, indicating that Zc3h12a is not involved in the regulation of the initial TLR signaling pathways (FIG. 15).

Example 5

Some CCCH-type zf proteins have been implicated in mRNA metabolism such as mRNA splicing, polyadenylation and the regulation of mRNA decay. Thus, it was assumed that Zc3h12a might play a role in the instability of mRNA, and this possibility was investigated using IL-6.

As described above, wild-type and Zc3h12a$^{-/-}$ macrophages were stimulated with LPS for 2 hours followed by actinomycin D treatment.

Figure 16:
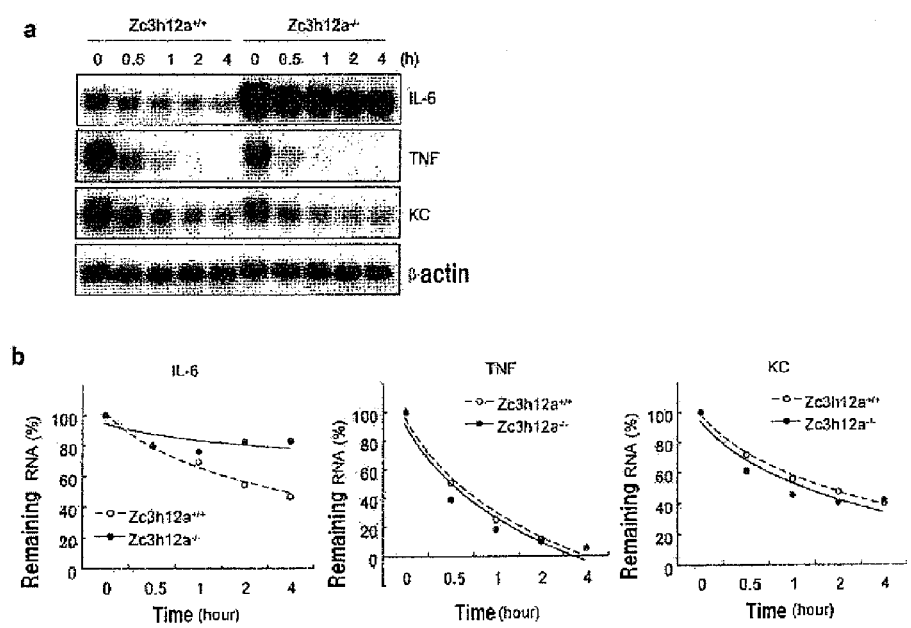
FIG. 16a is the results of Northern blot analysis for a destabilizing mechanism of Zc3h12a mRNA.
FIG. 16b is graphs showing the time course of remaining mRNA levels.

FIG. 16 shows that Zc3h12a destabilizes mRNA from a set of genes through their 3'-UTRs. FIG. 16a shows the results of RNA blot analysis of the expression of IL-6, TNF, KC and β-actin probes using extracted total RNA (10 µg). Similar results were obtained in three independent experiments. FIG. 16b is graphs showing the time course of remaining mRNA levels. In FIG. 16b, the autoradiograph was quantified and the ratio of IL-6, TNF, or Cxcl1 to Actb was used to determine remaining mRNA levels.

The half-life of IL-6 mRNA, but not of TNF or KC mRNA, increased in Zc3h12a$^{-/-}$ macrophages compared to that in wild-type cells (FIGS. 16a and 16b). These results indicate that Zc3h12a regulates IL-6 mRNA post-transcriptionally.

Example 6

Determination of Zc3h12a Responsive Region in 3'-UTR IL-6

To determine whether Zc3h12a expression controls IL-6 mRNA, the inventors transfected HEK293 cells stably expressing a tetracycline repressor protein fused to the transactivation domain of the viral transcription factor VP-16 (Tet-off 293 cells), with a plasmid containing the IL-6 coding sequence (CDS) with the 3'-untranslated region (UTR) sequence (pTREtight-IL6-CDS+3'-UTR) under the control of a tetracycline-responsive promoter (TRE) according to the method described in the instruction manual of Tet-On Gene Expression System (TAKARA). After treatment with doxycycline (Dox), the transcription of IL-6 mRNA was terminated and then the mRNA decayed in an incubation time-dependent manner (FIG. 17a). Overexpression of Zc3h12a greatly accelerated the degradation of IL-6 mRNA (FIGS. 17a and 17b). In contrast, Zc3h12a did not affect the expression of mRNA not harboring the 3'-UTR sequence (pTREtight-IL6-CDS) (FIGS. 17a and 17b).

Figure 17:
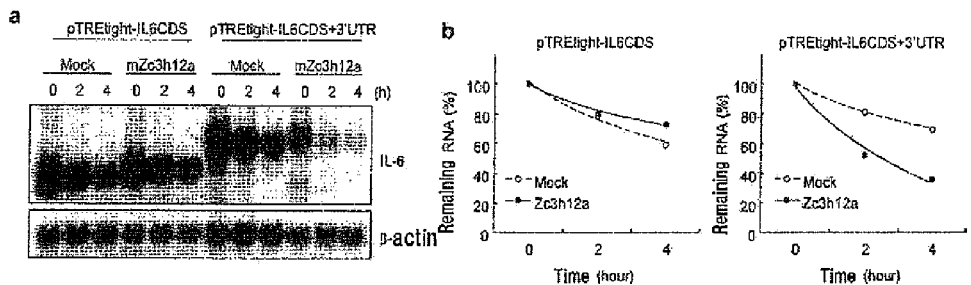
FIG. 17 is the results of Northern blot analysis (a) and a graph showing the time course of remaining mRNA levels (b). These experiments were carried out to determine a Zc3h12a responsive region in IL-6 3'-UTR by transfecting HEK293 Tet-off cells with plasmids.

FIG. 17 shows the results of Northern blot analysis (a) and remaining mRNA levels obtained by autoradiography (b), using RNA extracted from HEK293 Tet-off cells transfected with pTREtight-IL6-CDS or pTREtight-IL6-CDS+3'-UTR, together with a Zc3h12a expression plasmid or a control (empty) plasmid.

In FIG. 17a, the cells were subdivided 3 hours after transfection and incubated overnight. Total RNA was prepared after Dox (1 µg/ml) treatment, and IL-6 and β-actin RNA levels were determined by Northern blot analysis. In FIG. 17b, the autoradiograph was quantified and the ratio of IL-6 to Actb was used to determine remaining mRNA levels.

Figure 19:
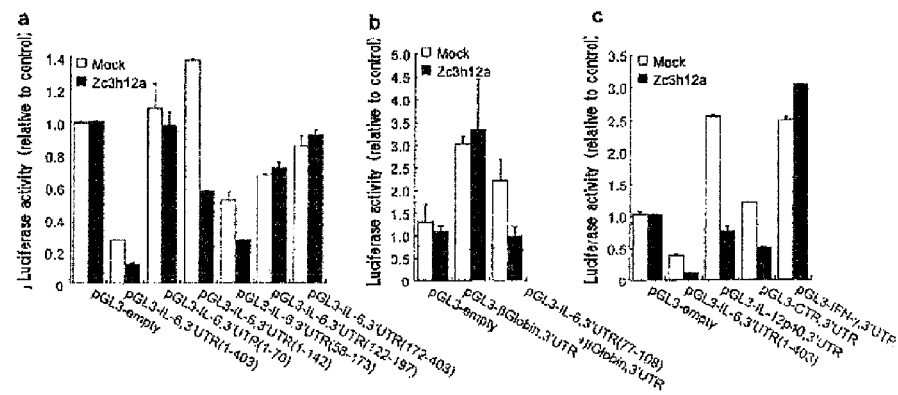
FIG. 19 is the measurement results of luciferase activity as a measure of RNA stability.

FIG. 19 is the measurement results of luciferase activity. Error bars indicate the standard deviation (S.D.) of duplicates. Similar results were obtained in three independent experiments.

In FIGS. 19a and b, HEK293 cells were transfected with pGL3 plasmids containing various sequences of IL-6 (FIG. 19a) 3'-UTR and/or β-globin (FIG. 19b) 3'-UTR, together with a Zc3h12a expression plasmid or a control (empty) plasmid, and the luciferase activity of the lysates of the cells was measured after 48 hours. In FIG. 19c, HEK293 cells were transfected with a pGL3 harboring the 3'-UTR for IL-6, IL-12p40, CTR, or interferon-γ, together with a Zc3h12a expression plasmid or a control (empty) plasmid, and the luciferase activity of the lysate of the cells was measured after 48 hours.

Figure 18:
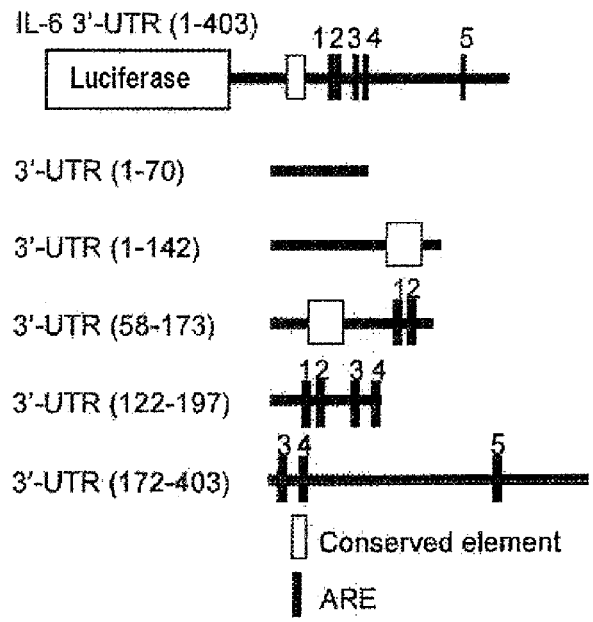
FIG. 18 is schematic views of IL-6 3'-UTR and its deletion constructs.

FIG. 18 is schematic views of IL-6 3'-UTR and its deletion constructs. Mouse IL-6 mRNA contains five adenine-uridine-rich elements (AREs) in its 3'-UTR (FIG. 18) (Zhao, W. et al. p38alpha stabilizes interleukin-6 mRNA via multiple AU-rich elements. J Biol Chem 283, 1778-85 (2008)).

Figure 20:
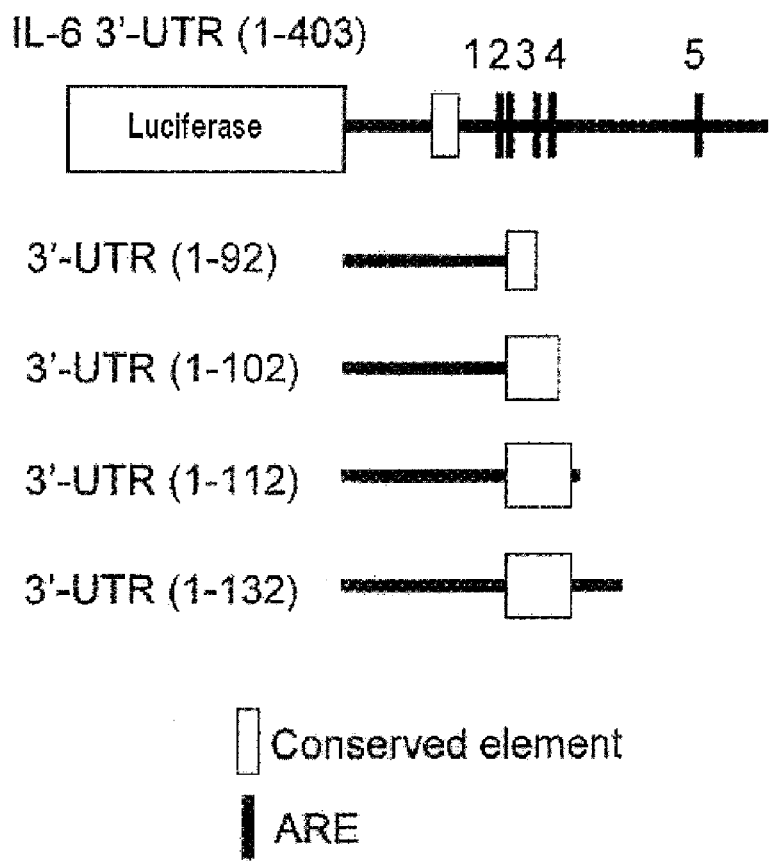
FIG. 20 is schematic views of IL-6 3'-UTR and its deletion constructs.

In addition, a conserved element (CE) between species comprising about 30 nucleotides was reported to be important for IL-6 mRNA destabilization (Paschoud, S. et al. Destabilization of interleukin-6 mRNA requires a putative RNA stem-loop structure, an AU-rich element, and the RNA-binding protein AUF1. Mol Cell Biol 26, 8228-41 (2006)). To investigate regions of the IL-6 3'-UTR that are critical for conferring Zc3h12a responsiveness, the inventors used a series of luciferase reporter constructs (pGL3) containing several regions of the IL-6 3'-UTR (FIG. 18). When full-length IL-6 3'-UTR (1-403) was inserted into the reporter, the luciferase activity decreased compared to that using the luciferase reporter alone. Co-expression of Zc3h12a further reduced the luciferase activity of pGL3-IL6 3'-UTR (1-403) (FIG. 19a). Whereas the luciferase activities of pGL3-IL6 3'-UTR (1-70) and pGL3-IL6 3'-UTR (172-403) were not altered by the expression of Zc3h12a, the luciferase activity of pGL3-IL6 3'-UTR (58-173) decreased in the presence of Zc3h12a. IL-6 3' UTR (58-173) contains two AREs and the CE (FIG. 19a). IL-6 3'-UTR (122-197) was not destabilized by Zc3h12a, suggesting that AREs are not critical for Zc3h12a-mediated destabilization of IL-6 mRNA. In contrast, IL-6 3'-UTR (1-142), which does not contain any ARE, was destabilized by Zc3h12a expression (FIG. 19a). By using a set of luciferase reporter constructs with shortened IL-6 3'-UTRs, the inventors found that IL-6 (1-102), but not IL-6 (1-92), was destabilized by Zc3h12a (FIG. 20). FIG. 20 is schematic views of IL-6 3'-UTR and its deletion constructs. Although the luciferase activity of pGL3-β-globin 3'-UTR was not affected by Zc3h12a expression, addition of IL-6 3'-UTR (77-108) to β-globin 3'-UTR conferred responsiveness to Zc3h12a (FIG. 19b). These results strongly suggested that the CE of IL-6 3'-UTR is important for Zc3h12a-mediated mRNA destabilization. The expression of Zc3h12a reduced the luciferase activity of the reporters with 3'-UTRs for IL-12p40 and a calcitonin receptor (CTR), but not that of the reporter with 3'-UTR for interferon-γ (FIG. 19c), indicating that IL-6, IL-12p40, and CTR mRNAs are directly regulated by Zc3h12a. Interferon-γ might be secondarily regulated by the overexpression of IL-12.

Example 7

Figure 21:
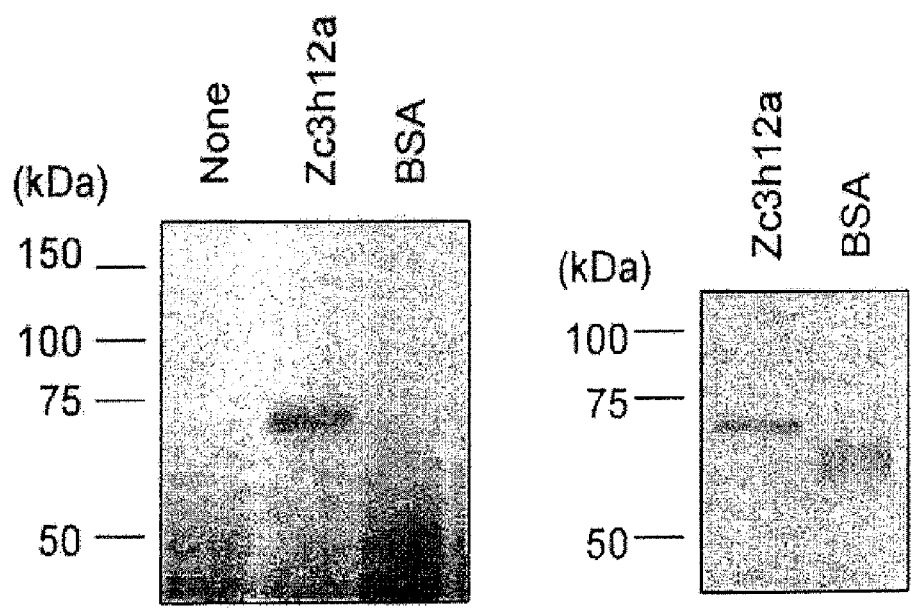
FIG. 21 is the examination results for binding to IL-6 3'-UTR (1-403) mRNA.

The inventors next examined whether Zc3h12a directly binds to RNA. FIG. 21 is the examination results by UV cross linking assay for binding to IL-6 3'-UTR (1-403) mRNA. Synthesized Zc3h12a protein, but not bovine serum albumin (BSA), bound to IL-6 3'-UTR (1-403) RNA transcribed in vitro, indicating that Zc3h12a harbors an RNA-binding capacity (FIG. 21).

Example 8

Role of CCCH Zf Motif in Destabilizing IL-6 mRNA

The inventors tested whether the CCCH sequence of Zc3h12a is critical for its role in IL-6 mRNA decay.

FIG. 22a is the results of Northern blot analysis for IL-6 expression in HEK293 Tet-off cells transfected with pTRE-tight-IL6-CDS+3'-UTR, together with an expression plasmid. encoding Flag-Zc3h12a or its mutant (C306R or ΔCCCH) in various amounts, and treated with Dox for the indicated time periods. FIG. 22b shows the expression levels of Zc3h12a mutant proteins determined by immunoblotting. The arrow in FIG. 22b indicates the expressed Zc3h12a protein.

Figure 23:
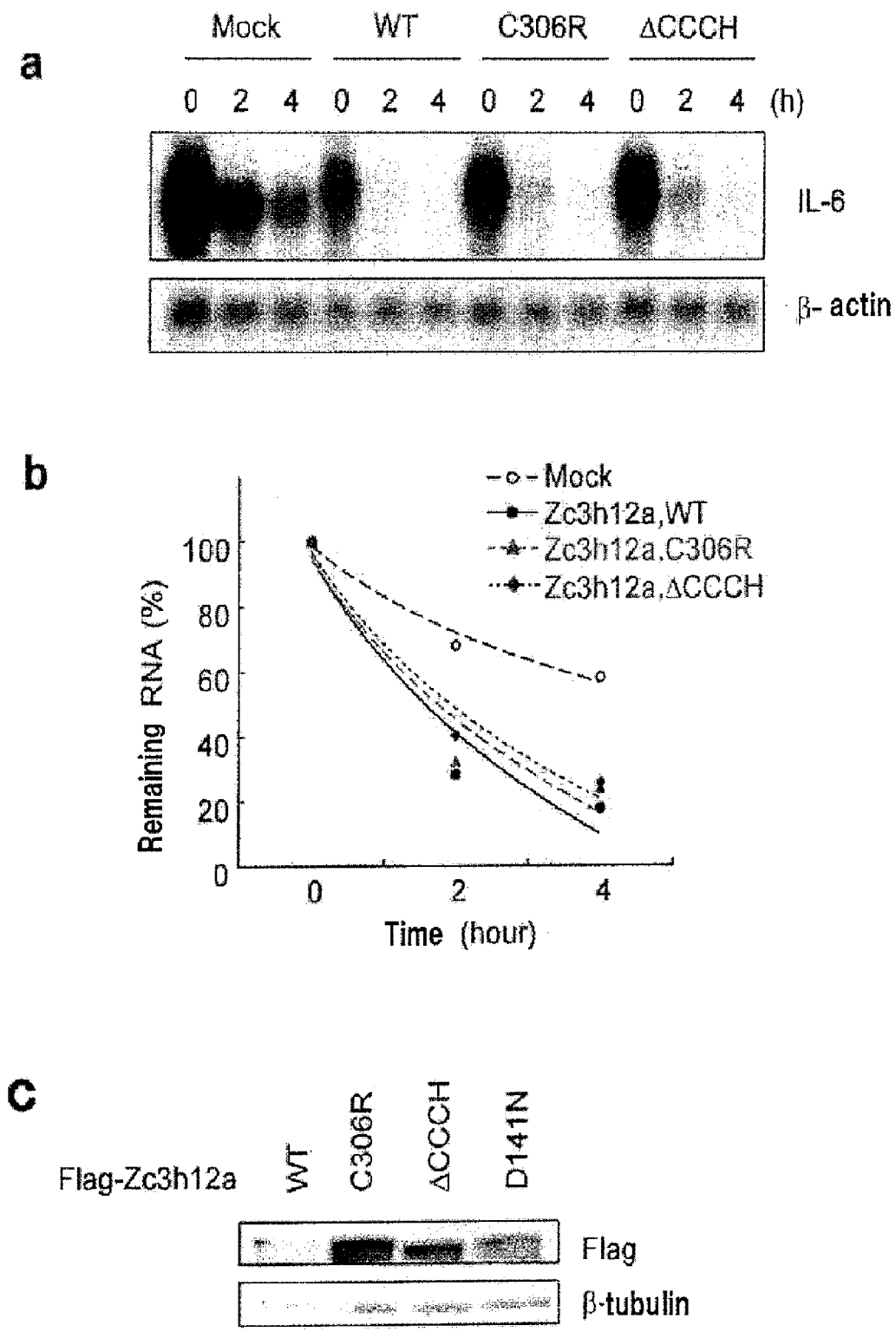
FIG. 23 is the results of Northern blot analysis (a) and immunoblot analysis (c) of IL-6 expression, and a graph showing the time course of remaining mRNA levels (b).

FIG. 23a is the results of Northern blot analysis for IL-6 expression in HEK293 Tet-off cells transfected with pTRE-tight-IL6-CDS+3'-UTR, together with an expression plasmid encoding Flag-Zc3h12a or its mutant (C306R or ΔCCCH), and treated with Dox for the indicated time periods. The autoradiograph was quantified and the ratio of IL-6 to Actb was used to determine remaining mRNA levels (FIG. 23b).

FIG. 23c is the results of immunoblot of the expression levels of Zc3h12a mutant proteins.

Figure 22:
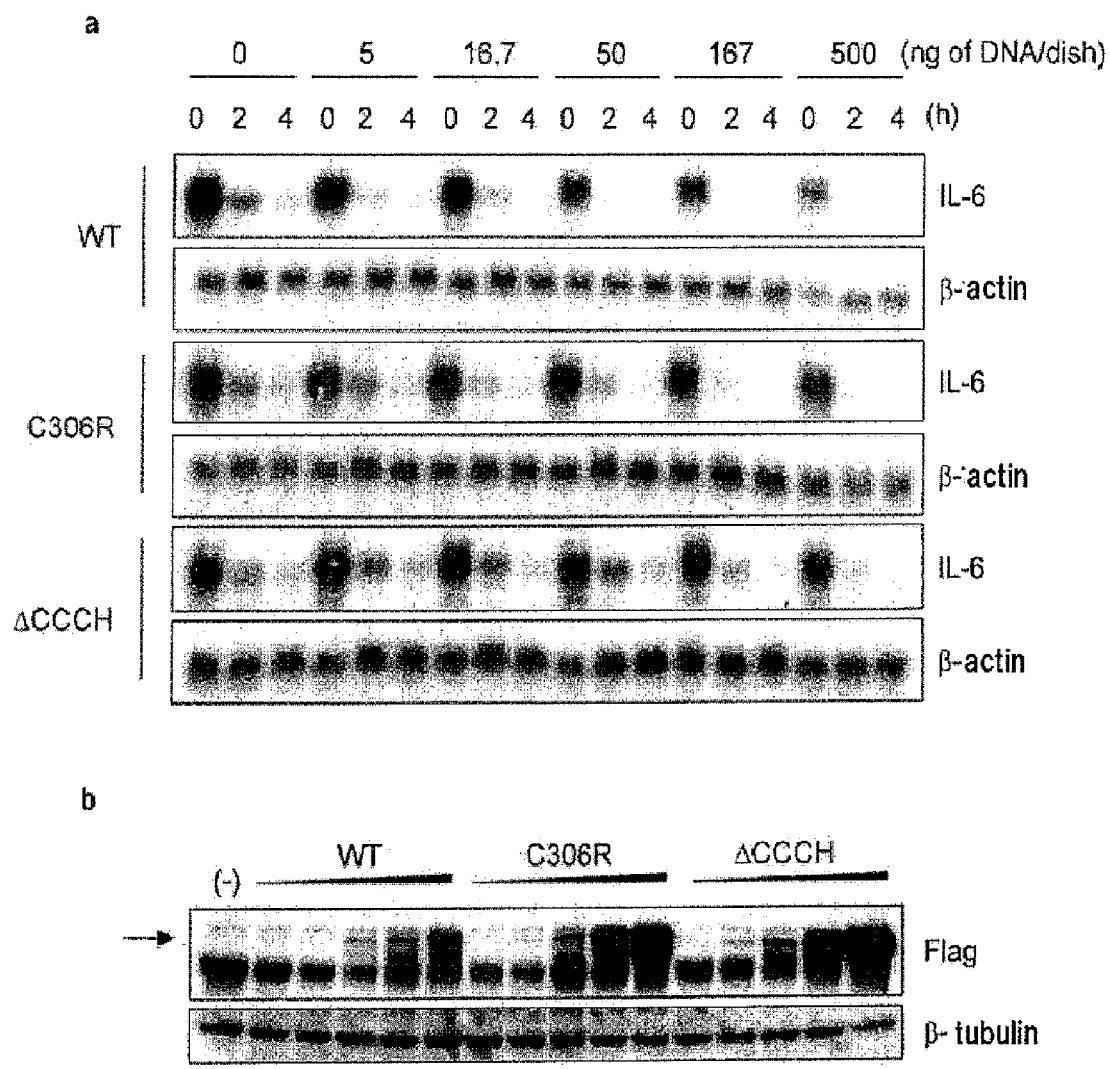
FIG. 22 is the results of Northern blot analysis (a) and immunoblot analysis (b) of Zc3h12a mutant protein expression levels.

The expression of Zc3h12a containing the C306R mutation in the CCCH zf domain, and Zc3h12a without the CCCH domain (lacking amino acids 306-322), could still destabilize IL-6 mRNA (FIGS. 23a to 23c), even though these mutant proteins had a reduced ability to degrade IL-6 mRNA when low amounts of the proteins were expressed (FIG. 22). These results indicate that the CCCH motif plays a role in the control of IL-6 mRNA decay.

Figures 24, 25:
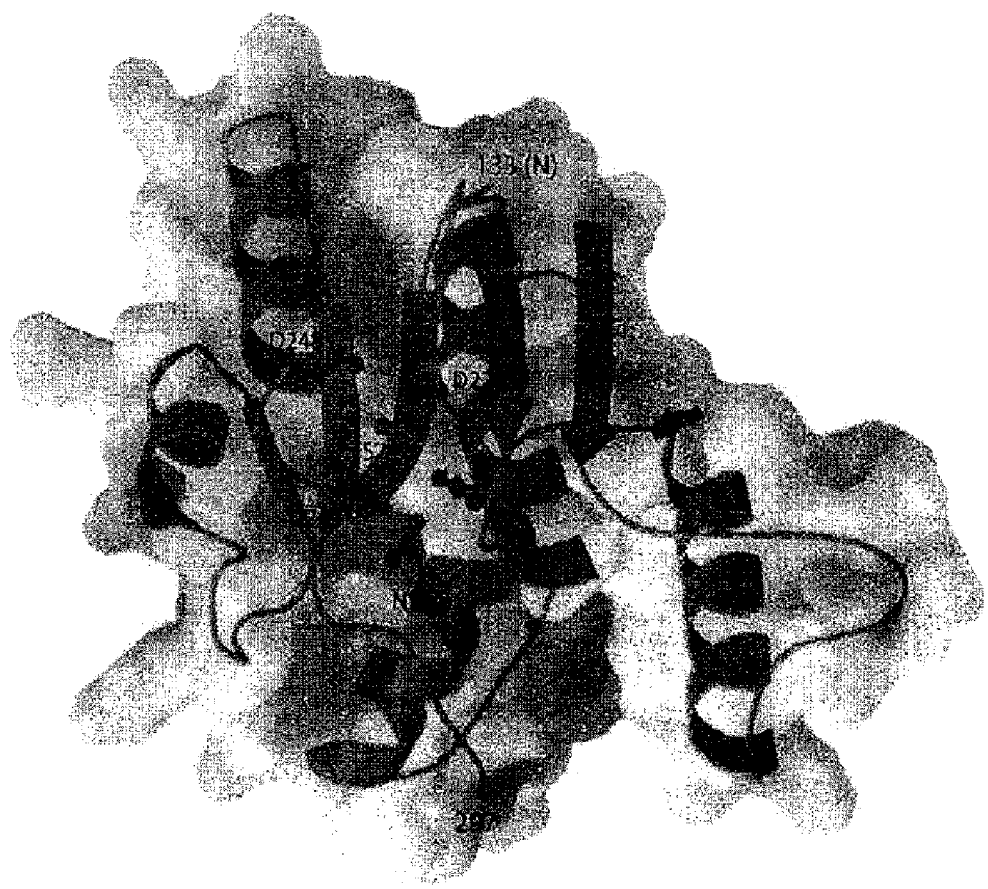

Sequence alignments of the N-terminals and CCCH domains in mouse and human Zc3h12a are shown in FIG. 24. In FIG. 24, the coloring parts are consensus sequences. The black dots (•) represent asparagine residues conserved in other PIN domain structures and the stars represent CCCH zinc fingers. The sequence alignments indicated that a conserved N-terminal domain (139-297) in Zc3h12a, just preceding the zf domain (300-324), shares remote homology to the PIN domain-like SCOP superfamily (FIG. 24). Structural modeling, followed by alignment to other PIN domain structures, revealed the presence of a conserved, negatively charged pocket—formed of Asp 141, Asn 144, Asp 226, Asp 244 and Asp 248—that is potentially important for magnesium binding and enzymatic activity (FIGS. 24 and 25). FIG. 25 is the structure model of the N-terminal domain of Zc3h12a, produced by structure modeling.

Figure 26:
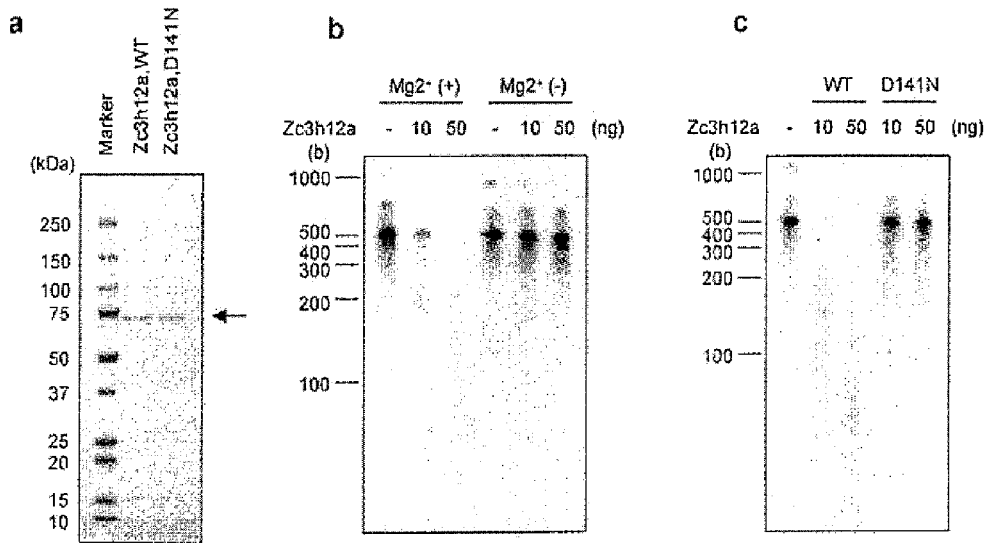
Figure 27:
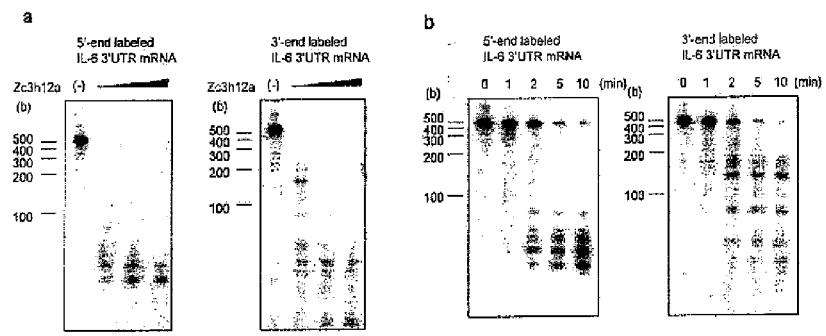

FIGS. 26 and 27 are the measurement results of the endoribonuclease activity of Zc3h12a. In these experiments, synthesized RNA was incubated with predetermined amounts (varying amounts) of the proteins. In FIGS. 26a to 26c, 27a, and 27b, the left lane is an RNA size marker. The expression levels of synthesized Zc3h12a and Zc3h12a (D141N) are shown in FIG. 26a, the ribonuclease activity of Zc3h12a in degrading IL-6 3'-UTR mRNA (1-403) in the presence or absence of 5 mM $Mg^{2+}$ is shown in FIG. 26b, and the ribonuclease activities of Zc3h12a and Zc3h12a (D141N) proteins are shown in FIG. 26c.

FIG. 27a is the results of in vitro cleavage assay of 5'- or 3'-end labeled IL-6 3'-UTR mRNA (1-403) with varying amounts of a recombinant Zc3h12a protein. FIG. 27b is the results of dynamic analysis of the ribonuclease activity of Zc3h12a. In the experiment shown in FIG. 27, 5'- or 3'-end labeled IL-6 3'-UTR mRNA (1-403) was incubated with a recombinant Zc3h12a protein for the indicated time periods.

FIG. 28a is the results of Northern blot analysis for the expression of IL-6. HEK293 Tet-off cells were transfected with pTREtight-IL6 full, together with Zc3h12a (D141N). The cells were then treated with Dox for the indicated time periods and the expression of IL-6 was measured by Northern blot analysis. FIG. 28b is graphs showing the time course of remaining mRNA levels.

Figure 28:
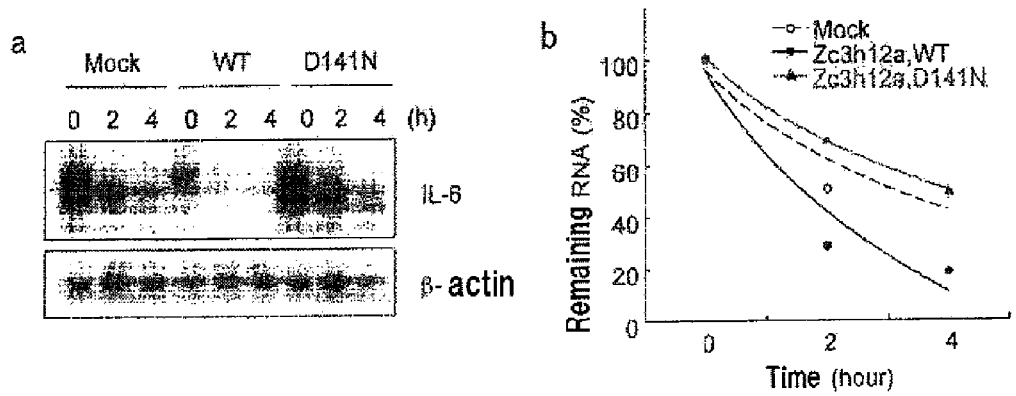
FIG. 28 is the results of Northern blot analysis (a) and a graph showing the time course of remaining mRNA levels (b).

From these results, the inventors presumed that the N-terminal domain of the Zc3h12a protein might be an ribonuclease, and that the synthesized Zc3h12a protein showed ribonuclease activity for IL-6 3'-UTR (1-403) mRNA in a $Mg^{2+}$-dependent manner (FIGS. 26a and 26b). Zc3h12a degraded 5'-labeled RNA and 3'-labeled RNA with similar kinetics, suggesting that Zc3h12a has endonuclease activity (FIG. 27). The activity of Zc3h12a seemed to be largely sequence-independent in vitro, because target RNAs with various sequences were degraded almost completely (data not shown). Furthermore, the Zc3h12a D141N mutant did not degrade RNA, indicating that the conserved pocket indeed functions as a ribonuclease active site (FIGS. 26a and 26c). The Zc3h12a D141N mutant failed to destabilize RNA containing IL-6 3'-UTR, indicating that the ribonuclease activity is essential for the function of Zc3h12a (FIGS. 23a and 28).

CONCLUSION

These experimental results clearly demonstrate that Zc3h12a is essential for the inhibition of the development of severe autoimmune responses culminating in the death of mice. Production of IL-6 and IL-12p40, but not TNF, was increased in Zc3h12a$^{-/-}$ macrophages due to mRNA decay failure. CCCH-type zinc-finger proteins have been shown to control mRNA decay by binding to the 3'-UTR. For example, tristetraprolin (TTP) and its homologues Zfp3611, Zfp3612 and Zfp3613, are critical for the decay of the mRNAs for TNF, GM-CSF, CXCL1 and the like (Anderson, P. Post-transcriptional control of cytokine production. Nat Immunol 9, 353-9 (2008); and Datta, S. et al. Tristetraprolin regulates CXCL1 (KC) mRNA stability. J Immunol 180, 2545-52 (2008)). Aged TTP$^{-/-}$ mice develop autoimmune arthritis owing to TNF production (Taylor, G. A. et al. A pathogenetic role for TNF alpha in the syndrome of cachexia, arthritis, and autoimmunity resulting from tristetraprolin (TTP) deficiency. Immunity 4, 445-54 (1996)). However, there is no report showing that TTP$^{-/-}$ cells produce increased amounts of IL-6 in response to TLR stimulation. Interestingly, the loss of Zc3h12a did not affect the expression of TNF mRNA in macrophages, indicating that TTP and Zc3h12a control mRNA decay for different cytokines. Zc3h12a targeted RNA sequences other than AREs, and the IL-6 AREs seem to be regulated by an unknown Zc3h12a-independent mechanism. Considering the profound pathological findings observed in Zc3h12.3.$^{-/-}$ mice, genes other than IL-6 and IL12p40 are probably critically involved in the pathogenesis too. Identification of Zc3h12a target genes in response to other stimuli or in other cell types will improve our knowledge of the whole mechanism of abnormalities observed in Zc3h12a$^{-/-}$ mice. Zc3h12a was recently reported to be a monocyte chemotactic protein-1 (MCP-1)-induced protein (Zhou, L. et al. Monocyte chemoattractant protein-1 induces a novel transcription factor that causes cardiac myocyte apoptosis and ventricular dysfunction. Circ Res 98, 1177-85 (2006)), and overexpression of the Zc3h12a protein was shown to suppress cytokine production in macrophages through inhibition of NF-κB activation (Liang, J. et al. A novel CCCH-zinc finger protein family regulates proinflammatory activation of macrophages. J Biol Chem 283, 6337-46 (2008)). However, the present experiments are inconsistent with this report, showing that Zc3h12a is involved in mRNA decay, but not in TNF regulation.

The Zc3h12a protein has intrinsic ribonuclease activity responsible for the decay of IL-6 mRNA. The mechanism is unique compared to the regulation of other ARE-mediated mRNA decay pathways. For instance, TTP has been shown to recruit deadenylases for removing polyA tails and facilitating the subsequent degradation of target mRNAs by exonucleases (Anderson, P., Post-transcriptional control of cytokine production. Nat Immunol 9, 353-9 (2008)). Thus, it is intriguing that Zc3h12a has endonuclease activity that, at least in vitro, does not show sequence specificity. The target specificity may be determined by binding partner(s) of Zc3h12a, or Zc3h12a may have a preferential sequence for degradation under certain conditions. The mechanism of how Zc3h12a induces decay of mRNAs is an intriguing topic for further exploration. The ribonuclease domain is conserved in four Zc3h12 family members, and the homologues of this protein family are found in metazoans such as *Drosophila melanogaster* (Gene ID: CG10889) and *Caenorhabditis elegans* (Gene ID: C30F12.1). Thus, regulation of mRNA by the ribonuclease domain and CCCH zf domain seems to be evolutionally conserved.

Another RING-type ubiquitin ligase protein containing a CCCH zf motif called roquin is essential for suppressing autoimmunity by controlling the expression of the ICOS costimulatory molecule (Vinuesa, C. G. et al. A RING-type ubiquitin ligase family member required to repress follicular helper T cells and autoimmunity. Nature 435, 452-8 (2005)). Roquin and several microRNAs seem to share an ICOS 3'-UTR RNA segment for suppressing its degradation (Yu, D. et al. Roquin represses autoimmunity by limiting inducible T-cell co-stimulator messenger RNA. Nature 450, 299-303 (2007)). Given that each CCCH zf protein seems to have target mRNA specificity and 60 CCCH-type zf proteins have been identified in the mammalian genome (Liang, J. et al. Genome-wide survey and expression profiling of CCCH-zinc finger family reveals a functional module in macrophage activation. PLoS ONE 3, e2880 (2008)), control of mRNA decay might be as important as the control of transcription in terms of regulation of innate immune responses.

The invention claimed is:

1. A process comprising the step of an antigen with at least one member selected from the group consisting of a Zc3h12a gene inhibitor and a Zc3h12a protein inhibitor; wherein the antigen is selected from the group consisting of a food allergen, a house dust allergen, a pollen allergen, an animal hair allergen, a bacterium, a virus, and a parasite.

2. The process according to claim 1, further comprising mixing the antigen with another immunoadjuvant.

3. The method of claim 1, wherein the bacterium is a *rickettsia* bacterium.

* * * * *

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Synthetic construct; oligonucleotide for primer

<400> SEQUENCE: 1
atatgagtga cccttgtgga acgaagc                                           27

<210> SEQ ID NO 2
<211> LENGTH: 27
<212> TYPE: DNA
<213> ORGANISM: Artificial Sequence
```

```
<220> FEATURE:
<223> OTHER INFORMATION: Synthetic construct; oligonucleotide for primer

<400> SEQUENCE: 2
tctgtacaca gcatacatgt gtcctcc                                          27
```